(12) United States Patent
Wang et al.

(10) Patent No.: US 9,353,132 B2
(45) Date of Patent: May 31, 2016

(54) BORON-BASED 4-HYDROXYTAMOXIFEN AND ENDOXIFEN PRODRUGS AS TREATMENT FOR BREAST CANCER

(71) Applicant: XAVIER UNIVERSITY OF LOUISIANA, New Orleans, LA (US)

(72) Inventors: Guangdi Wang, New Orleans, LA (US);
Shilong Zheng, New Orleans, LA (US);
Quan Jiang, New Orleans, LA (US);
Qiu Zhong, New Orleans, LA (US);
Qiang Zhang, New Orleans, LA (US)

(73) Assignee: XAVIER UNIVERSITY OF LOUISIANA, New Orleans, LA (US)

( * ) Notice: Subject to any disclaimer, the term of this patent is extended or adjusted under 35 U.S.C. 154(b) by 147 days.

(21) Appl. No.: 14/382,356

(22) PCT Filed: Mar. 5, 2013

(86) PCT No.: PCT/US2013/029059
§ 371 (c)(1),
(2) Date: Sep. 2, 2014

(87) PCT Pub. No.: WO2013/134230
PCT Pub. Date: Sep. 12, 2013

(65) Prior Publication Data
US 2015/0080339 A1    Mar. 19, 2015

Related U.S. Application Data

(60) Provisional application No. 61/634,680, filed on Mar. 5, 2012.

(51) Int. Cl.
*C07F 5/02* (2006.01)
*A61K 31/69* (2006.01)
*C07F 5/04* (2006.01)

(52) U.S. Cl.
CPC ............... *C07F 5/027* (2013.01); *A61K 31/69* (2013.01); *C07F 5/02* (2013.01); *C07F 5/025* (2013.01); *C07F 5/04* (2013.01)

(58) Field of Classification Search
CPC ............ C07F 5/027; C07F 5/025; C07F 5/02; C07F 5/04; A61K 31/69
See application file for complete search history.

(56) References Cited

U.S. PATENT DOCUMENTS

| | | | |
|---|---|---|---|
| 3,288,806 | A | 11/1966 | De Wald |
| 4,536,516 | A | 8/1985 | Harper et al. |
| 5,554,628 | A | 9/1996 | Bryant et al. |

FOREIGN PATENT DOCUMENTS

| | | |
|---|---|---|
| CA | 2348853 A1 | 11/2002 |
| CN | 1163567 A | 10/1997 |

OTHER PUBLICATIONS

Rickert et al. "Synthesis and Characterization of Fluorescent 4-Hydroxytamoxifen Conjugates with Unique Antiestrogenic Properties" Bioconjugate Chemistry, 2010, vol. 21, pp. 903-910.*
Jung et al., "Boron-Based 4-Hydroxytamoxifen Bioisosteres for Tamoxifen Resistant Breast Cancer." ACS Medicinal Chemistry Letters, 3(5) (2012) 392-396, XP055195676.
Rickert et al., "Synthesis and Characterization of Fluorescen Conjugates with Unique Antiestrogenic Properties." Bioconjugate Chemistry, 21(5) (2010) 903-910, XP055083672.
European Search Report dated Jun. 26, 2015, issued in PCT/US2013029059.
International Search Report from corresponding PCT/US2013/029059, mailed Jun. 27, 2013.
Michael, Storyet al., "Signal Transduction During Adoptosis; Implications for Cancer Therapy", Frontiers in Bioscience, vol. 3, pp. 365-375, Mar. 23, 1998.
Philipp, Y. Maximov et al., "Structure-Function Relationships of Estrogenic Triphenylethylenes Related to Endoxifen and 4-Hydroxytamoxifen", J. Med. Chem., vol. 53, pp. 3273-3283, Mar. 24, 2010.
Jiang et al., "Boron-Based 4-Hydroxytamoxifen Bioisosteres for Treatment of de Novo Tamoxifen Resistant Breast Cancer." ACS Medicinal Chemistry Letters, 2012, vol. 3, pp. 392-396.

* cited by examiner

*Primary Examiner* — Joseph Kosack
(74) *Attorney, Agent, or Firm* — McBee Moore Woodward & Vanik IP, LLC

(57) ABSTRACT

The present disclosure relates to boron-based 4-hydroxytamoxifen and endoxifen prodrugs and the synthesis of the same. Further, the present disclosure teaches the utilization of the boron-based 4-hydroxytamoxifen and endoxifen prodrugs in a treatment for breast cancer.

41 Claims, 14 Drawing Sheets

BORON-BASED 4-HYDROXYTAMOXIFEN AND ENDOXIFEN PRODRUGS AS TREATMENT FOR BREAST CANCER

CROSS REFERENCE TO RELATED APPLICATIONS

This application is a §371 National Stage Application of PCT/US2013/029059, which claims priority to U.S. Provisional Patent Application No. 61/634,680, filed under 35 U.S.C. §111(b) on Mar. 5, 2012, which is hereby incorporated by reference in its entirety.

BACKGROUND

1. Field of the Disclosure

The present disclosure relates to novel 4-hydroxytamoxifen and endoxifen prodrugs and the synthesis of the same. Further, the present disclosure teaches the utilization of the novel 4-hydroxytamoxifen and endoxifen prodrugs in a treatment for breast cancer.

The treatment of breast cancer patients with the novel 4-hydroxytamoxifen and endoxifen prodrug compounds taught herein can particularly be beneficial in those patients presenting intrinsic (de novo) resistance to tamoxifen, due to deficient cytochrome P450 2D6 enzyme (CYP2D6) or drug interactions that inhibit the activity of CYP2D6. Further still, the present novel compounds are beneficial to treat ER positive breast cancer patients who can benefit from the use of lower doses of endocrine therapy for reduced side effects.

2. Description of Related Art

Tamoxifen has been the mainstay hormonal therapy for breast cancer that expresses the estrogen receptor (ER+) since the 1980s. Early descriptions of the tamoxifen compound can be found in U.S. Pat. Nos. 3,288,806 and 4,536,516, both of which are herein incorporated by reference in their entireties.

Nearly 70% of all diagnosed breast tumors are classified as ER+, most of which initially respond to tamoxifen treatment. (see ref. 1). However, approximately 8% of breast cancer patients present intrinsic resistance to tamoxifen (see ref. 2) mainly because these patients do not have a functional cytochrome P450 2D6 enzyme (CYP2D6), encoded by the polymorphic CYP2D6 gene, that is responsible for converting tamoxifen to its more potent metabolites, 4-hydroxytamoxifen (4-OHT) and endoxifen. (see ref. 3).

Indeed, breast cancer mortality was significantly increased in patients with CYP2D6 null-allele compared to wild type patients. (see ref. 4). Jordan and co-workers first reported that high first-pass metabolism of tamoxifen led to a significant increase in its activity and characterized the first active primary metabolite, 4-OHT (see refs. 5-6), which showed 30- to 100-fold greater potency than tamoxifen in inhibiting estrogen-dependent cell proliferation. (see ref. 7-9).

The predominant biotransformation route, demethylation of tamoxifen to form N-desmethyltamoxifen is catalyzed by the P450 enzyme CYP3A4/5. (see ref. 10). This major primary metabolite has potency similar to tamoxifen. It is then converted into the more potent secondary metabolite endoxifen exclusively by CYP2D6. On the other hand, the same CYP2D6 is required for the formation of 4-OHT, which is equally or more potent than endoxifen. While the hydroxylation at the 4C-position depends on CYP2D6, the biotransformation from 4-hydroxytamoxifen to endoxifen does not. In fact, it has been shown that CYP3A4/5 is primarily responsible for this metabolic route of 4-OHT demethylation leading to endoxifen formation. Thus, both endoxifen and 4-hydroxytamoxifen represent desirable alternatives to tamoxifen for breast cancer patients lacking the active form of the cytochrome P450 2D6 enzyme CYP2D6. (see refs. 11-15).

Despite this understanding, effective synthetic 4-OHT and endoxifen prodrugs remain unavailable, and there remains a need in the art for these compounds.

BRIEF SUMMARY

The present disclosure provides novel boron-based 4-hydroxytamoxifen (4-OHT) and endoxifen prodrugs that have been discovered to have potent inhibitory effects on cell-proliferation of breast cancer cells that are estrogen receptor positive (ER+). The efficacies of the novel compounds presented herein are comparable to, or better than, tamoxifen and its active tamoxifen metabolite, 4-hydroxytamoxifen. Consequently, the present novel boron-based prodrug compounds address an important need in the art.

Thus, in an embodiment, the boron-based 4-hydroxytamoxifen (4-OHT) and endoxifen prodrugs of the present disclosure are compounds of the formula (I):

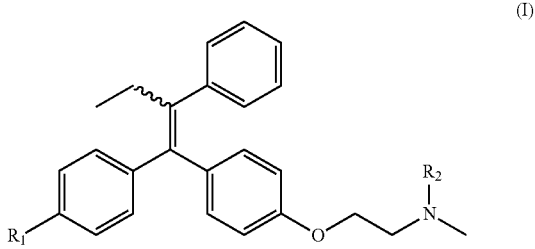

wherein
$R_1$ is

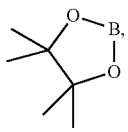

$KF_3B$, $(HO)_2B$, $NaF_3B$,

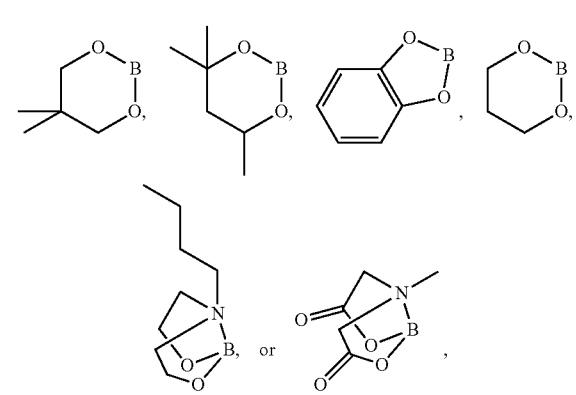

wherein the $R_1$ substituent point of attachment is on the Boron atom;
and
$R_2$ is methyl or hydrogen.

In particular embodiments of the compounds of formula (I), $R_2$ is methyl. These compounds are referred to collectively as boron-based 4-OHT prodrugs.

In other embodiments of the compounds of formula (I), $R_2$ is hydrogen. These compounds are referred to collectively as boron-based endoxifen prodrugs.

In a particularly preferred embodiment, the born-based 4-OHT prodrugs are compounds having the following structures, denoted prodrugs 1, 2, and 3:

Prodrug 1

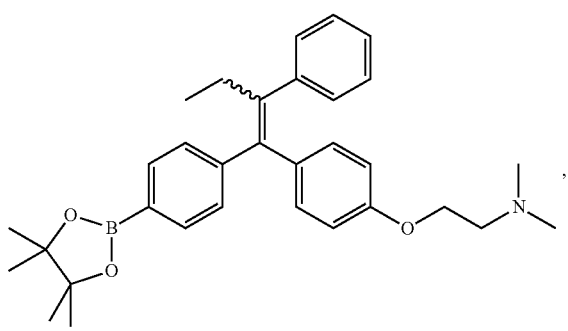

Prodrug 2

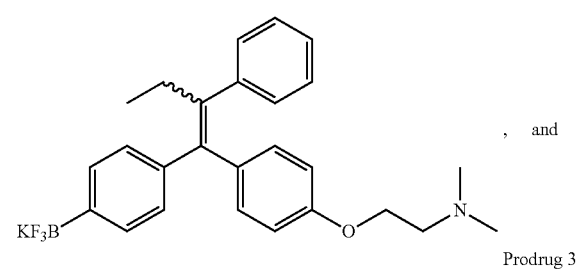

, and

Prodrug 3

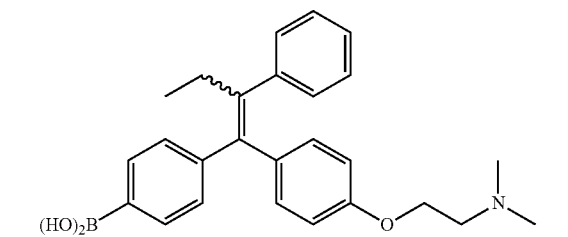

In a particularly preferred embodiment, the born-based endoxifen prodrug is a compound having the following structure, denoted prodrug 11:

Prodrug 11

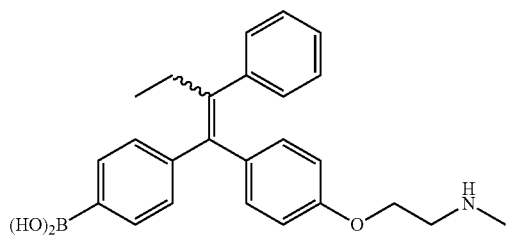

In another embodiment, the boron-based 4-OHT prodrug compound is selected from the group consisting of N,N-Dimethyl-2-(4-(2-phenyl-1-(4-(4,4,5,5-tetramethyl-1,3,2-dioxaborolan-2-yl)phenyl)but-1-en-1-yl)phenoxy)ethanamine, Potassium (4-(1-(4-(2-(dimethylamino) ethoxy)phenyl)-2-phenylbut-1-en-1-yl)phenyl)trifluoroboronate, (4-(1-(4-(2-(Dimethylamino)ethoxy)phenyl)-2-phenylbut-1-en-1-yl)phenyl)boronic acid, Sodium (4-(1-(4-(2-(dimethylamino) ethoxy)phenyl)-2-phenylbut-1-en-1-yl) phenyl)trifluoroboronate, 2-(4-(1-(4-(5,5-Dimethyl-1,3,2-dioxaborinan-2-yl)phenyl)-2-phenylbut-1-en-1-yl) phenoxy)-N,N-dimethylethanamine, N,N-Dimethyl-2-(4-(2-phenyl-1-(4-(4,4,6-trimethyl-1,3,2-dioxaborinan-2-yl) phenyl)but-1-en-1-yl)phenoxy)ethanamine, 2-(4-(1-(4-(Benzo[d][1,3,2]dioxaborol-2-yl)phenyl)-2-phenylbut-1-en-1-yl)phenoxy)-N,N-dimethylethanamine, 2-(4-(1-(4-(1,3,2-Dioxaborinan-2-yl)phenyl)-2-phenylbut-1-en-1-yl) phenoxy)-N,N-dimethylethanamine, (4-(1-(4-(2-(Dimethylamino) ethoxy)phenyl)-2-phenylbut-1-en-1-yl) phenyl)N-methyliminodiacetic acid boronate, and (4-(1-(4-(2-(Dimethylamino) ethoxy)phenyl)-2-phenylbut-1-en-1-yl) phenyl) N-butyldiethanol amine boronate.

In yet another embodiment, the boron-based endoxifen prodrug compound is selected from the group consisting of (4-(1-(4-(2-(Methylamino) ethoxy)phenyl)-2-phenylbut-1-en-1-yl)phenyl)boronic acid, Potassium (4-(1-(4-(2-(methylamino) ethoxy)phenyl)-2-phenylbut-1-en-1-yl)phenyl)trifluoroborate, N-Methyl-2-(4-(2-phenyl-1-(4-(4,4,5,5-tetramethyl-1,3,2-dioxaborolan-2-yl)phenyl)but-1-en-1-yl) phenoxy)ethanamine, Sodium (4-(1-(4-(2-(methylamino) ethoxy)phenyl)-2-phenylbut-1-en-1-yl)phenyl) trifluoroboronate, 2-(4-(1-(4-(5,5-Dimethyl-1,3,2-dioxaborinan-2-yl)phenyl)-2-phenylbut-1-en-1-yl) phenoxy)-N-methylethanamine, N-Methyl-2-(4-(2-phenyl-1-(4-(4,4,6-trimethyl-1,3,2-dioxaborinan-2-yl)phenyl)but-1-en-1-yl)phenoxy)ethanamine, 2-(4-(1-(4-(Benzo[d][1,3,2] dioxaborol-2-yl)phenyl)-2-phenylbut-1-en-1-yl)phenoxy)-N-methylethanamine, 2-(4-(1-(4-(1,3,2-Dioxaborinan-2-yl)phenyl)-2-phenylbut-1-en-1-yl)phenoxy)-N-methylethanamine, (4-(1-(4-(2-(Methylamino) ethoxy) phenyl)-2-phenylbut-1-en-1-yl)phenyl)N-methyliminodiacetic acid boronate, and (4-(1-(4-(2-(Methylamino) ethoxy)phenyl)-2-phenylbut-1-en-1-yl) phenyl)N-butyldiethanol amine boronate.

In an embodiment, the disclosure provides for a pharmaceutical composition for the treatment of breast cancer, wherein said composition comprises a novel boron-based 4-OHT prodrug in an amount effective for the therapeutic treatment of breast cancer.

In yet other embodiments, the disclosure provides for a pharmaceutical composition for the treatment of breast cancer, wherein said composition comprises a novel boron-based endoxifen prodrug in an amount effective for the therapeutic treatment of breast cancer.

The pharmaceutical compositions of the present disclosure can be in any form known to those of skill in the art. For instance, in some embodiments the pharmaceutical compositions are in a form of a product for oral delivery, said product form being selected from a group consisting of a concentrate, dried powder, liquid, capsule, pellet, and pill. In other embodiments, the pharmaceutical compositions of the disclosure are in the form of a product for parenteral administration including intravenous, intradermal, intramuscular, and subcutaneous administration. The pharmaceutical compositions disclosed herein may also further comprise carriers, binders, diluents, and excipients.

Also, in other aspects, the present disclosure relates to new boron-based prodrug compounds and their pharmaceutically acceptable salts; pharmaceutical compositions comprising the new boron-based prodrug compounds, either alone or in combination with at least one additional therapeutic agent, with a pharmaceutically acceptable carrier; and uses of the new boron-based prodrug compounds, either alone or in combination with at least one additional therapeutic agent, in the prophylaxis or treatment of cellular proliferative diseases, such as cancer, and in particular cancer presenting as breast cancer, or any cancer dependent upon an estrogen receptor pathway. The combination with an additional therapeutic agent may take the form of combining the new boron-based prodrug compounds with a known chemotherapeutic agent.

Moreover, the presently taught 4-hydroxytamoxifen and endoxifen prodrugs undergo facile oxidative cleavage of the boron-aryl carbon bond to yield 4-hydroxytamoxifen or endoxifen, the desired drug forms, after incubation with ER+ breast cancer cells. Thus, the presently disclosed prodrugs can be useful in the prevention and treatment of ER+ breast cancer without the need to have functional enzymatic activities of CYP2D6. Thus, some preferred embodiments of the present disclosure relate to methods of treatments for breast cancer utilizing the prodrugs disclosed herein. The methods taught herein may relate to administering the disclosed prodrugs to a patient in need thereof.

Furthermore, the present disclosure in some embodiments provides methods for the treatment of any type of cancer that is dependent upon an estrogen receptor (ER) pathway, said method comprising administering the disclosed prodrugs to a patient in need thereof.

It is a further object of the disclosure to provide novel 4-OHT and endoxifen prodrug compounds, methods of synthesizing the prodrug compounds, methods of manufacturing the prodrug compounds, and methods of using the prodrug compounds. Particularly contemplated uses for the novel prodrug compounds, include for example: treatment of cancers, including breast cancer, and cancer cells that express the estrogen receptor.

Another object of the disclosure is to provide a composition, for example a pharmaceutical composition, comprising at least one boron-based prodrug in an amount effective for preventing or minimizing the development or growth of a cancer, which may be a primary cancer or a secondary (metastatic) lesion thereof. The cancer may be breast cancer, gastric carcinoma, ovarian cancer, pancreatic cancer, stomach cancer, non-small-cell lung cancer, or any cancer involving the hormone signaling pathway.

A further object of the disclosure is a kit, comprising a composition containing at least one novel boron-based prodrug for preventing or minimizing the development or growth of breast cancer. The composition of the kit may comprise at least one carrier, at least one binder, at least one diluent, at least one excipient, at least one other therapeutic agent, or mixtures thereof.

Also provided are methods of preventing or treating cancer or tumor growth in a mammal comprising administering to the mammal an effective amount of a composition comprising at least one novel boron-based prodrug analog, and determining if the development or growth of cancer has been prevented, minimized, or reversed.

The methods for treating cancer with the novel boron-based prodrug compounds disclosed herein, especially breast cancer, may be effectuated by administering a therapeutically effective amount of the prodrug to a patient in need thereof, this therapeutically effective amount may comprise administration of the prodrug to the patient at 1 mg/kg/day, 5 mg/kg/day, 10 mg/kg/day, 20 mg/kg/day, 30 mg/kg/day, and 40 mg/kg/day. Alternatively, amounts ranging from about 0.001 mg/kg/day to about 0.01 mg/kg/day, or about 0.01 mg/kg/day to about 0.1 mg/kg/day, or about 0.1 mg/kg/day to about 1 mg/kg/day, or about 1 mg/kg/day to about 10 mg/kg/day, or about 10 mg/kg/day to about 100 mg/kg/day are also contemplated.

The present methods also contemplate the administration of the present prodrugs in combination with at least one other known anti-cancer active agent for tumor treatment.

In certain aspects, the at least one novel boron-based prodrug analog has a purity of ≥75%, ≥80%, ≥85%, ≥90%, ≥95%, ≥96%, ≥97%, or ≥98%, and preferably ≥99%.

While certain novel features of this invention shown and described below are pointed out in the annexed claims, the invention is not intended to be limited to the details specified, since a person of ordinary skill in the relevant art will understand that various omissions, modifications, substitutions, and changes in the forms and details of the invention illustrated and in its operation may be made without departing in any way from the spirit of the present invention. No feature of the invention is critical or essential unless it is expressly stated as being "critical" or "essential."

These and other features, aspects, and advantages of embodiments of the present disclosure will become better understood with regard to the following description, claims, and accompanying drawings explained below.

Figure 1:
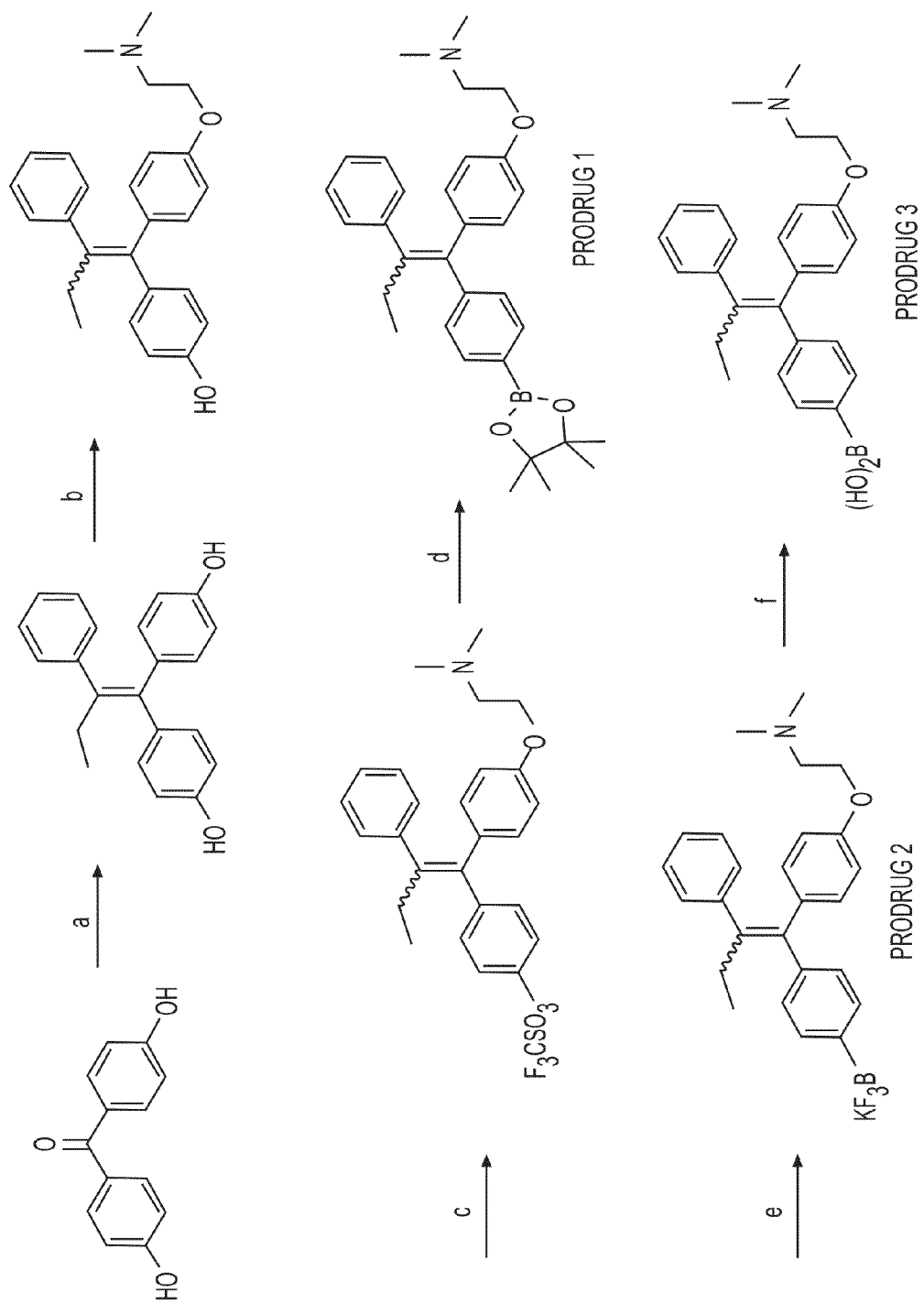
FIG. 1. Synthesis of Boron-4-OHT Prodrugs

The synthesis of boron-based 4-hydroxytamoxifen bioisosteres is outlined in FIG. 1. 4-hydroxytamoxifen was synthesized by McMurry reaction between 4,4'-dihydroxybenzophenone and propiophenone and subsequent monoalkylaton with 2-(dimethylamino)ethylchloride hydrochloride in the presence of cesium carbonate in DMF. Then, 4-hydroxytamoxifen was converted into the triflate by the reaction with trifluoromethanesulfonic anhydride. The 1,1'-bis(diphenylphosphino)ferrocene-palladium(II)dichloride dichloromethane complex (PdCl$_2$(dppf))-catalyzed borylation of the triflate gave the pinacolyl boronate ester of tamoxifen derivative (Prodrug 1) using diboron reagent in the presence of KOAc. The reaction of the pinacolyl boronate ester 1 with potassium bifluoride formed the potassium trifluoroborate of tamoxifen (Prodrug 2). The free boronic acid prodrug 3 was obtained successfully via hydrolysis of prodrug 2 using trimethylsilyl chloride.

The reagents and conditions denoted in the figure are as follows: (a) propiophenone, TiCl$_4$, Zn, THF, reflux; (b) 2-(dimethylamino) ethylchloride hydrochloride, Cs$_2$CO$_3$, DMF, 70-80° C.; (c) (CF$_3$SO$_2$)$_2$O, pyridine, CH$_2$Cl$_2$, 0° C.-rt; (d)

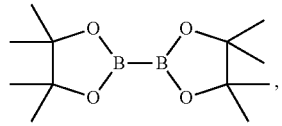

PdCl$_2$(dppf), KOAc, dioxane, reflux; (e) KHF$_2$, MeOH/H$_2$O, room temperature; (f) (CH$_3$)$_3$SiCl, CH$_3$CN, H$_2$O, under room temperature.

Figure 2:
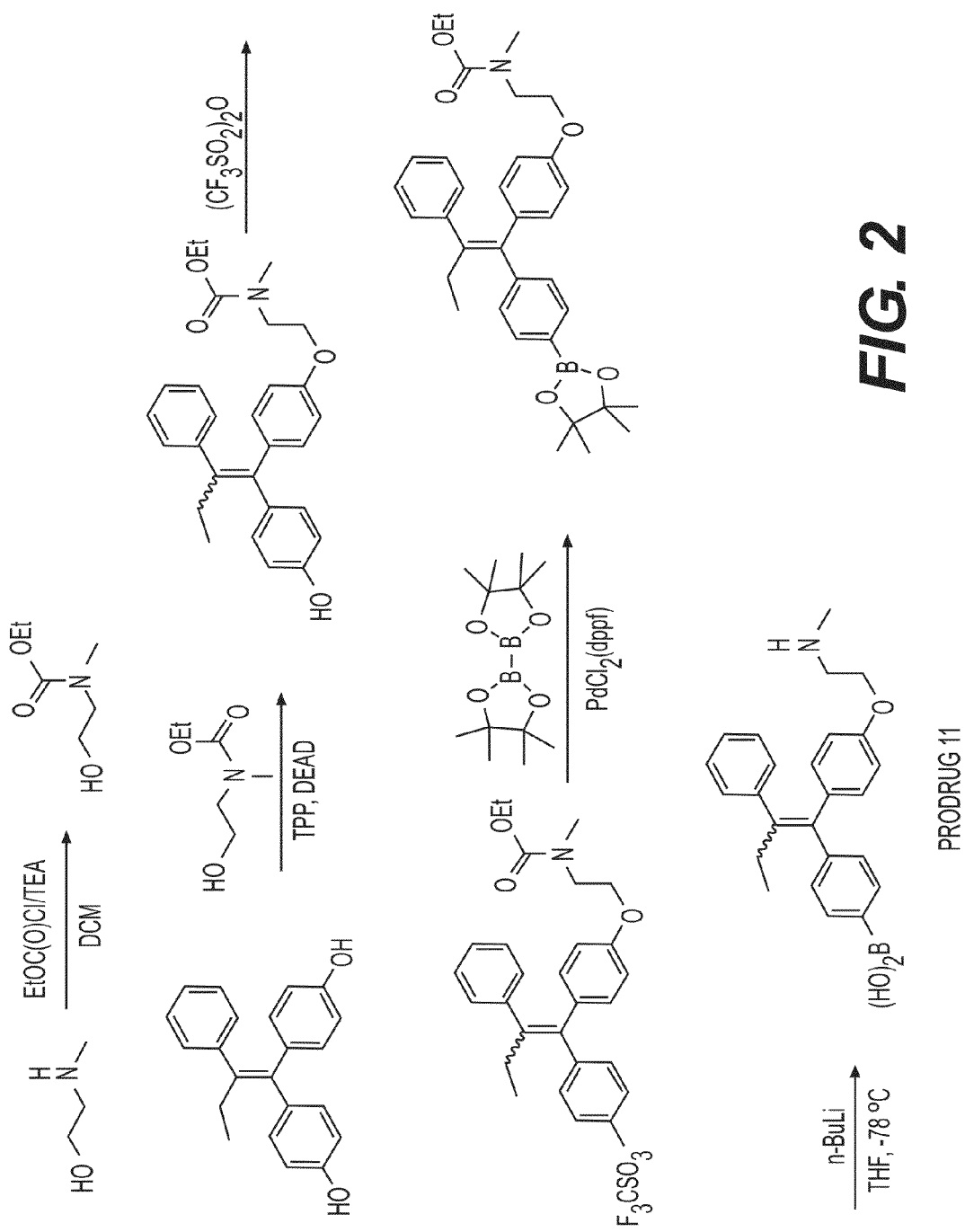

FIG. 2. Synthesis of Boron-Endoxifen Prodrugs

The synthesis of boron-based endoxifen bioisosteres is outlined in FIG. 2. The monoalkylation of 4,4'-(2-phenylbut-1-ene-1,1-diyl)diphenol by ethyl(2-hydroxyethyl)(methyl) carbamate which was prepared by reacting the alcohol with ethylchloroformate/triethylamine (EtOC(O)Cl/TEA) in dichloromethane (DCM) gave ethyl(2-(4-(1-(4-hydroxyphenyl)-2-phenylbut-1-en-1-yl)phenoxy)ethyl)(methyl)(carbamate) under Mitsunobu reaction with triphenylphosphine (TPP) and diethylazodicarboxylate (DEAD) as catalysts in dichloromethane. Then, ethyl(2-(4-(1-(4-hydroxyphenyl)-2-phenylbut-1-en-1-yl)phenoxy)ethyl)(methyl)(carbamate) was converted into the triflate by reacting with trifluoromethanesulfonic anhydride (($CF_3SO_2)_2O$) in dichloromethane. The $PdCl_2$(dppf)-catalyzed borylation of the triflate gave the pinacolyl boronate ester using a diboron reagent in the presence of KOAc. The removal of ethoxycarbonyl moiety from the pinacolyl boronate ester with n-butyllithium at −78° C. afforded the endoxifen Prodrug 11.

Figure 3:
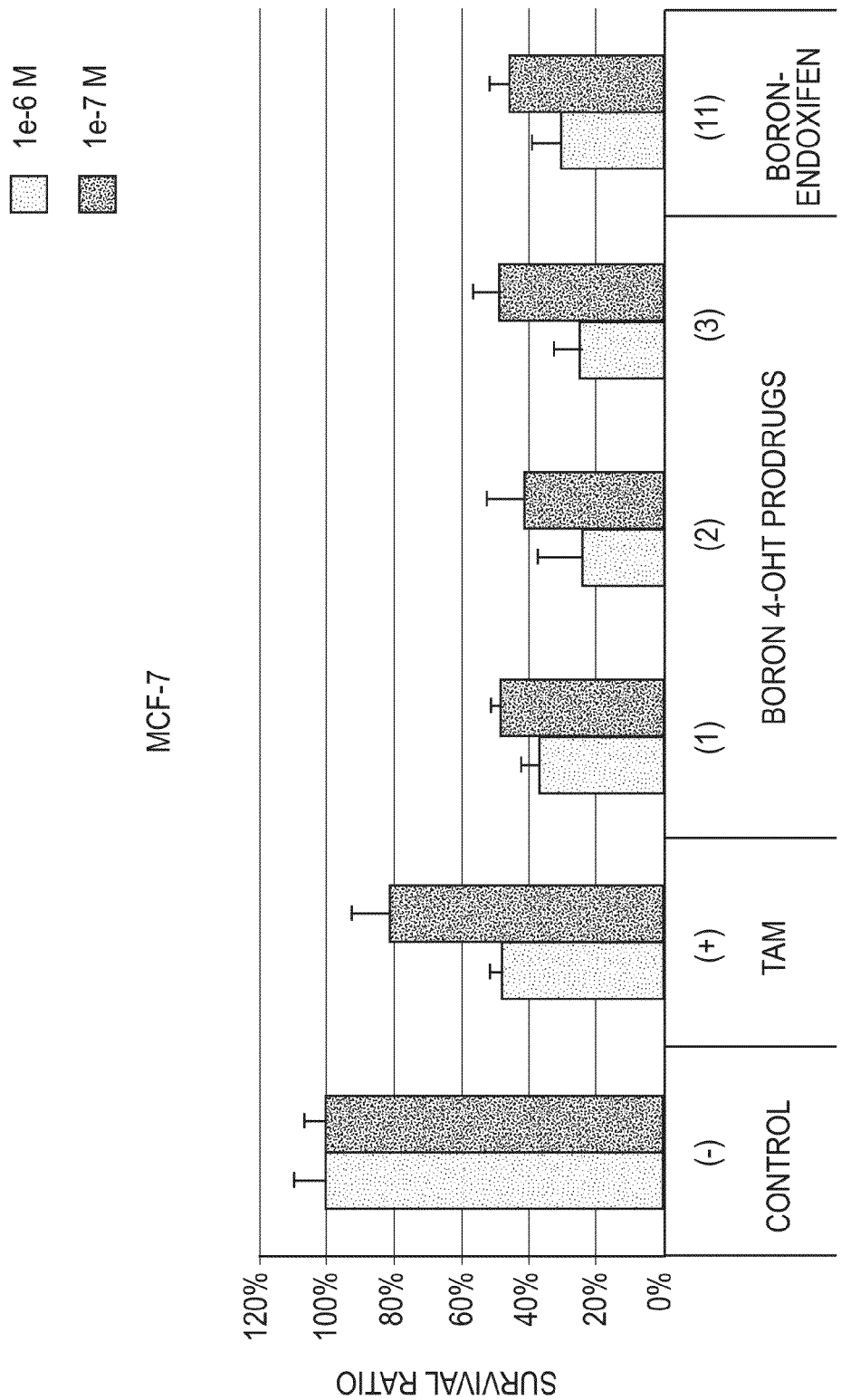

FIG. 3. In Vitro MCF-7 Breast Cancer Inhibition by Prodrugs 1, 2, and 3

FIG. 3 shows the inhibition of MCF-7 breast cancer cells in vitro by prodrugs 1, 2, and 3, at two doses of $10^{-7}$ and $10^{-6}$ M, respectively. MCF-7 is a human breast adenocarcinoma cell line commonly accepted in the art as useful for in vitro breast cancer studies because it has retained several ideal characteristics particular to mammary epithelium. These characteristics include the ability to process estrogen (in the form of estradiol) via estrogen receptors in the cell cytoplasm. This makes the MCF-7 cell line an estrogen receptor (ER) positive control cell line. Tamoxifen inhibited MCF-7 cell survival and growth by 18% and 52% at $10^{-7}$ M and $10^{-6}$ M, respectively. In comparison, the pinacolyl boronate ester prodrug (1), showed 52% growth inhibition at $10^{-7}$ M, and 63% at $10^{-6}$ M. The trifluoroborate prodrug (2) demonstrated growth inhibition on MCF-7 cells by 59% at $10^{-7}$ M and 76% inhibition at $10^{-6}$ M concentration. Prodrug 3 inhibited cell growth with comparable efficacies at the two doses, with a 51% inhibition at $10^{-7}$ M and 75% inhibition at $10^{-6}$ M. The endoxifen prodrug 11 also exhibited greater anti-proliferative efficacy than tamoxifen.

Figure 4:
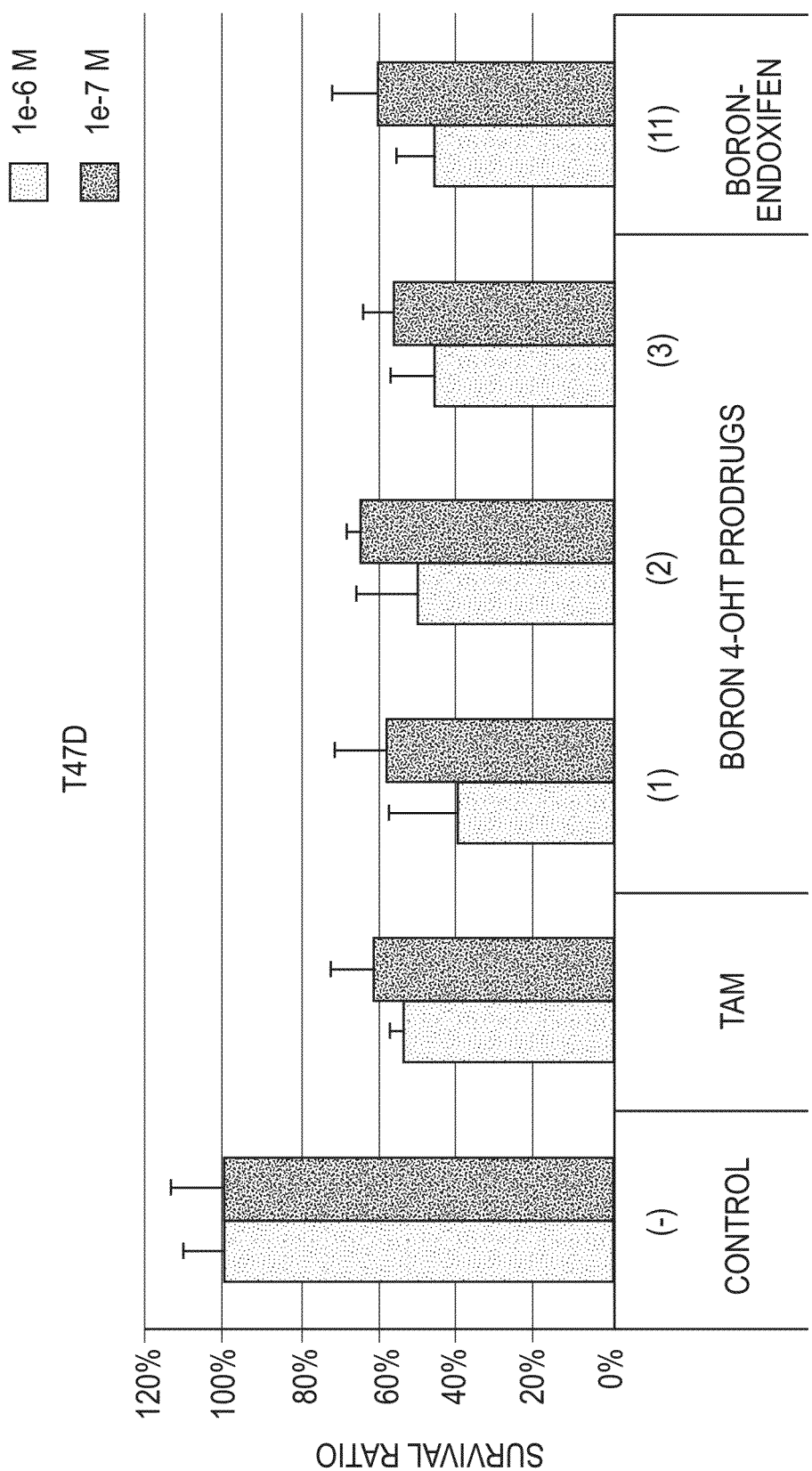

FIG. 4. In Vitro T47D Breast Cancer Inhibition by Prodrugs 1, 2, and 3

FIG. 4 shows the inhibition of T47D breast cancer cells in vitro by prodrugs 1, 2, and 3 at two doses of $10^{-7}$ and $10^{-6}$ M, respectively. The T47D cell line is also an ER positive control cell line. At $10^{-6}$ M, the prodrugs 1, 2, and 3 achieved 60%, 50%, and 54% growth inhibitions of the T47D cells, respectively, compared to 48% inhibition by Tamoxifen. At $10^{-7}$ M, the prodrugs 1, 2, and 3 achieved 42%, 38%, and 44% growth inhibitions of the T47D cells, respectively, compared to 39% inhibition by Tamoxifen. The boron-endoxifen prodrug (11) demonstrated 40% inhibition at $10^{-7}$M and 53% inhibition at $10^{-6}$ M. These results clearly demonstrate the effectiveness of the 4-OHT prodrugs as antiestrogens in inhibiting the growth of ER+ breast cancer cells represented by T47D cells.

Figure 5A:
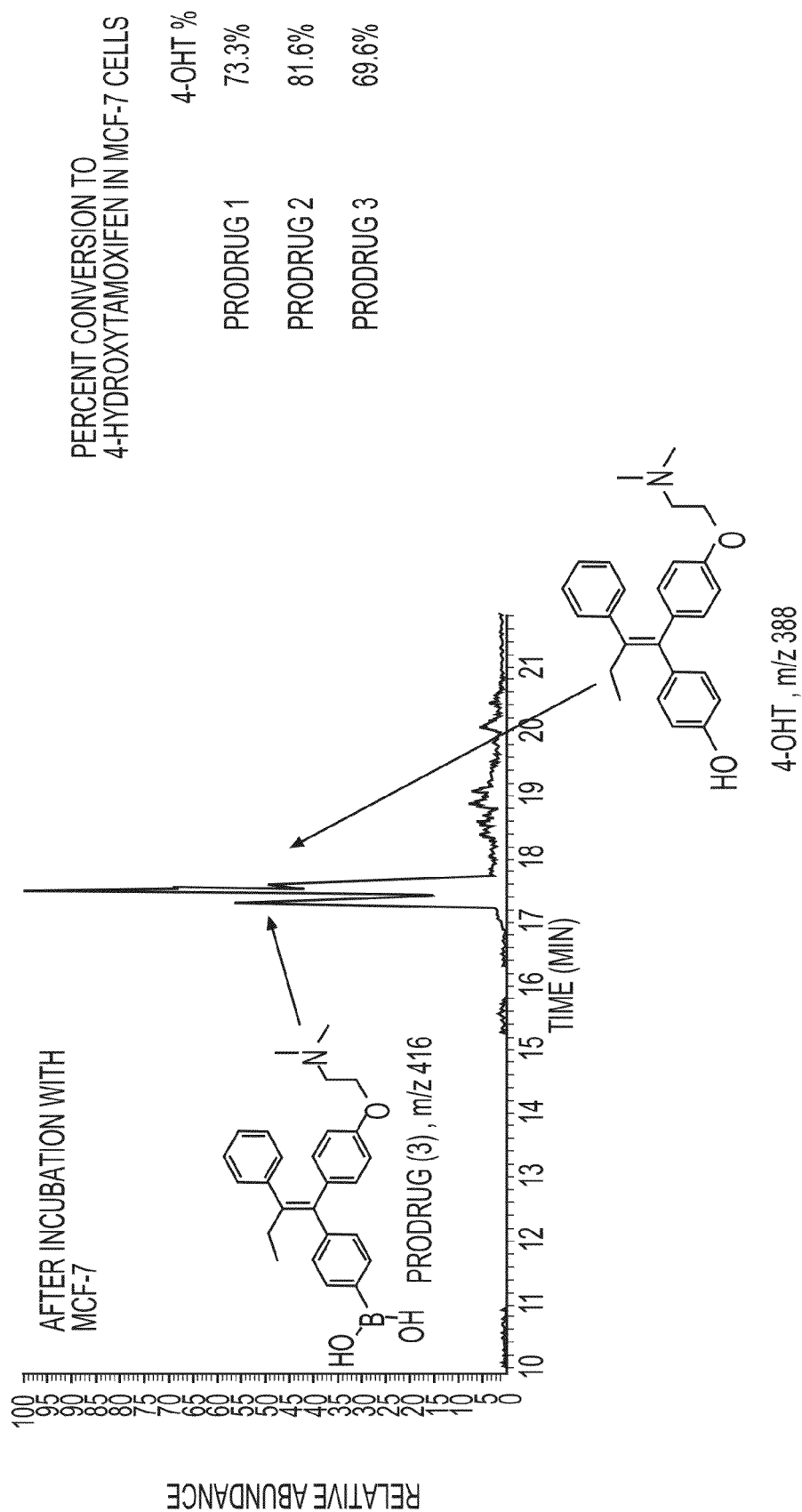
Figure 5B:
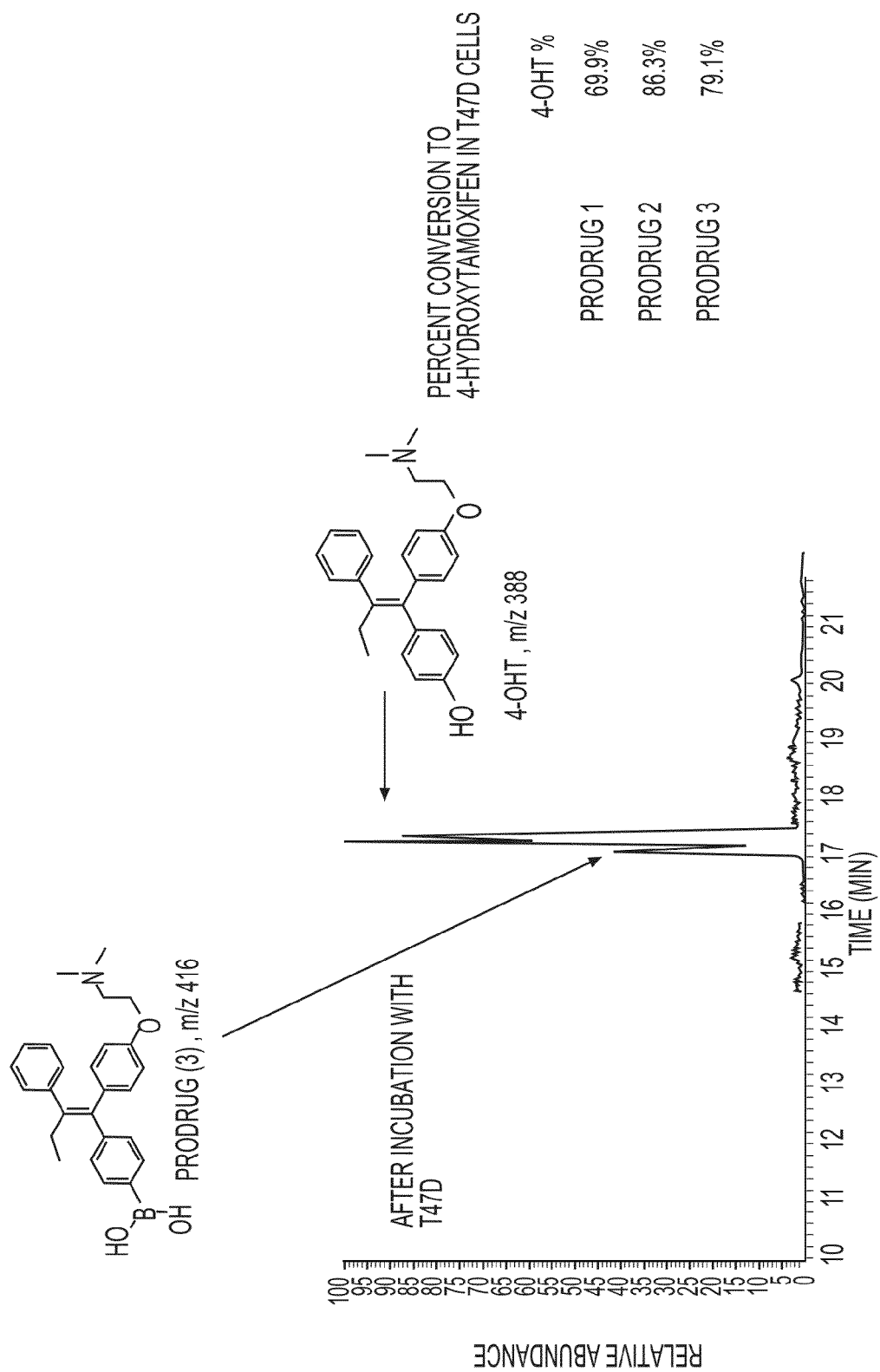

FIG. 5. Liquid Chromatography-Mass Spectrometry

FIG. 5 shows the relative concentrations of prodrugs and their common oxidative product, 4-hydroxytamoxifen, as determined by LC-MS/MS after incubation with (A) MCF-7 cells and (B) T47D cells.

Figure 6:
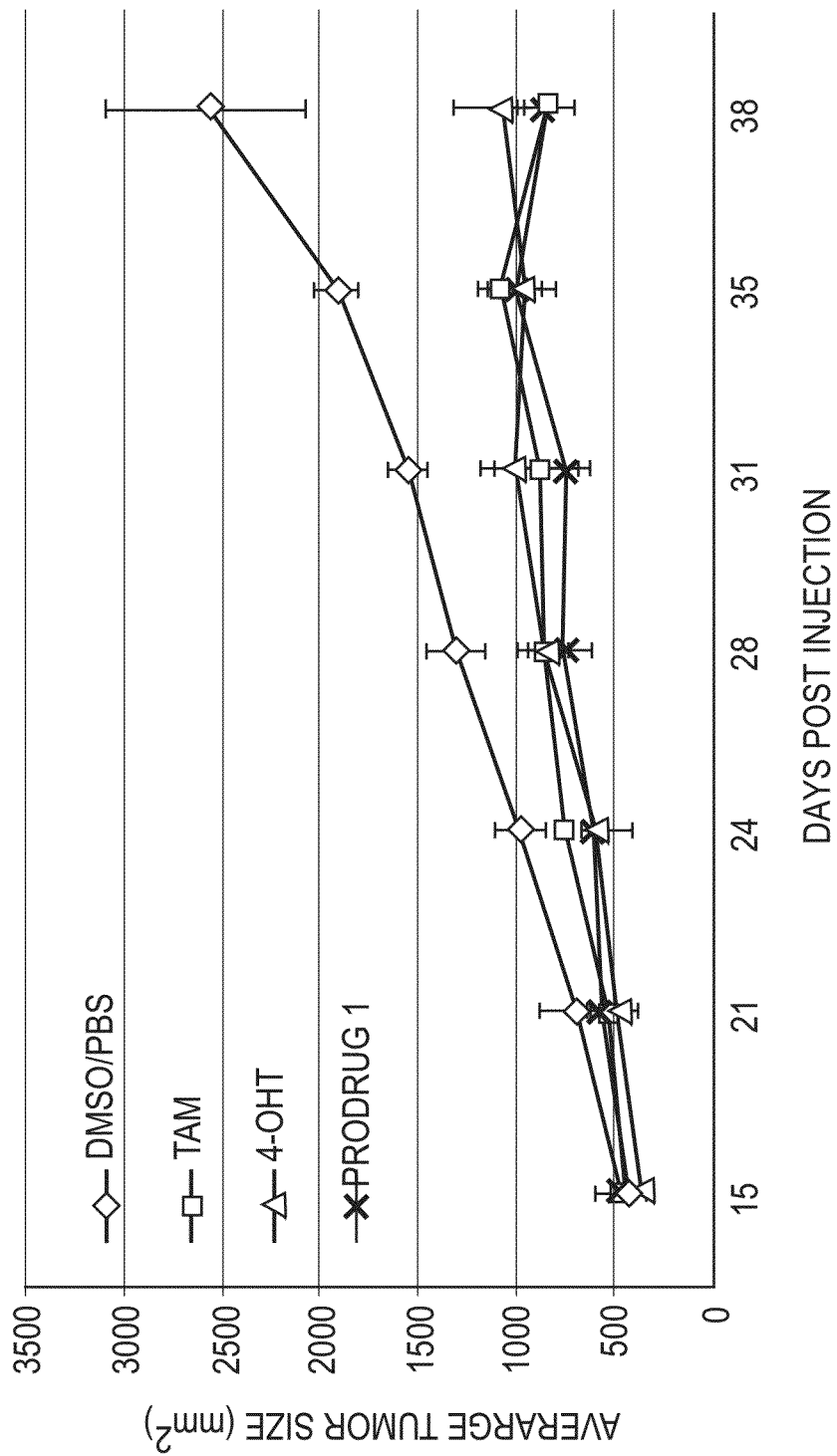

FIG. 6. In Vivo Testing of Prodrug 1 on MCF-7 Cell Tumorigenesis

FIG. 6 shows anti-estrogenic effects of prodrug 1 on MCF-7 cell tumorigenesis in vivo. 4-6 week old ovariectomized female Nu/Nu mice were injected bilaterally in the mammary fat pad (MFP) with $5 \times 10^6$ MCF-7 cells in matrigel (reduced factor). All animals were implanted with a 17β-estradiol pellet (0.72 mg, 60-day release) subcutaneously in the lateral area of the neck at the time of cell injection. Tumors were allowed to form and at day 15 post cell injection mice were randomized into groups (n=5). Animals were treated daily with intraperitoneal (i.p.) injections of either vehicle (1:5 DMSO/PBS), Tamoxifen, 4-hydroxytomoxifen, or prodrug 1 (5 mg/kg/animal). Tumor size was measured 3 times weekly using digital calipers. Data are represented as mean tumor volume±SEM.

Figure 7:
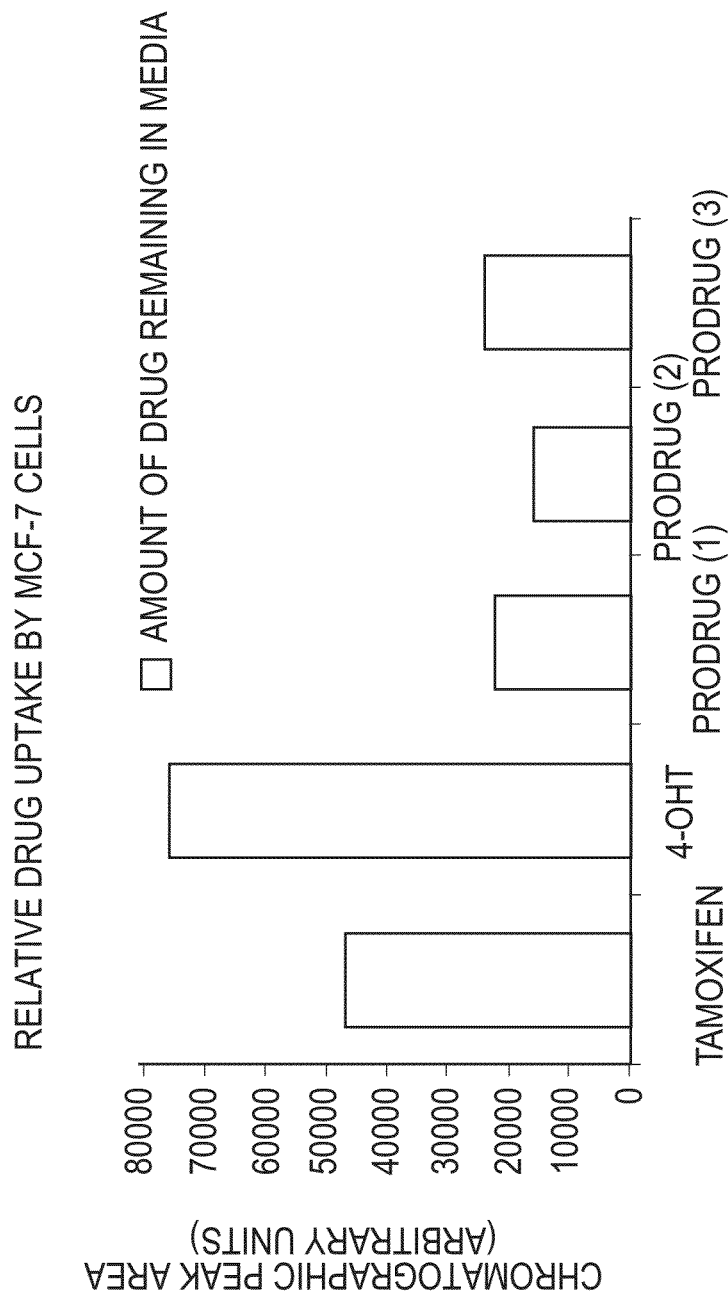

FIG. 7. Relative Drug Uptake by MCF-7 Cells

FIG. 7 shows increased uptake of boronic prodrugs by the breast cancer cell. The modification of 4-OHT structure by incorporation of the boron-carbon bond is likely responsible for improved cellular uptake of the prodrugs. To compare the relative uptake of the prodrugs vs. Tamoxifen and 4-OHT, we measured the concentrations of the remaining drugs in media after a 6-day period of incubation with MCF-7 cells. Results show that the concentration of 4-OHT in media is approximately 2-4 times higher than those of prodrugs 1, 2, and 3. While it is also possible that the boron prodrugs may have their own antiestrogenic activities, our experimental data suggest that the prodrugs were taken up more efficiently by the cancer cells.

Figure 8:
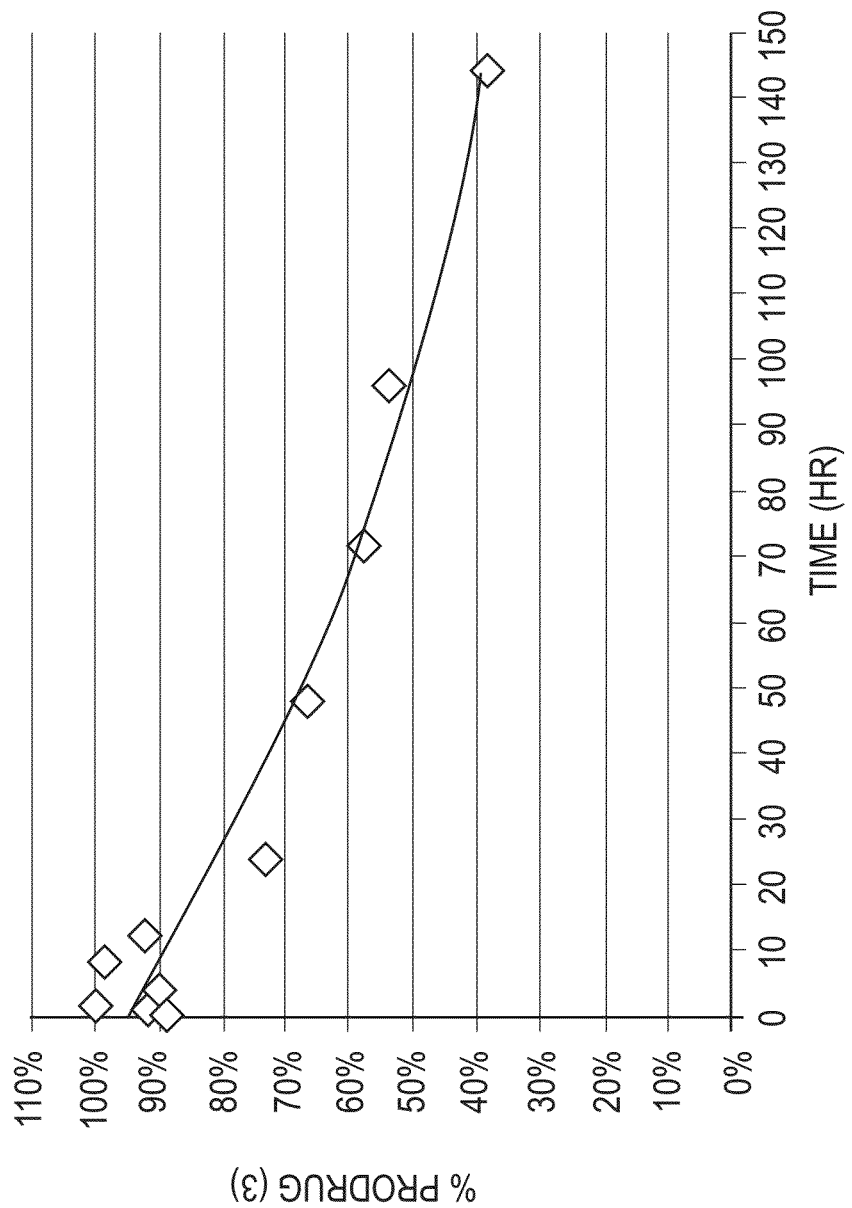

FIG. 8. Kinetic Stability of Prodrug 3

FIG. 8 shows the time dependent conversion of prodrug (3) to 4-OHT in MCF-7 cell culture.

Figure 9:
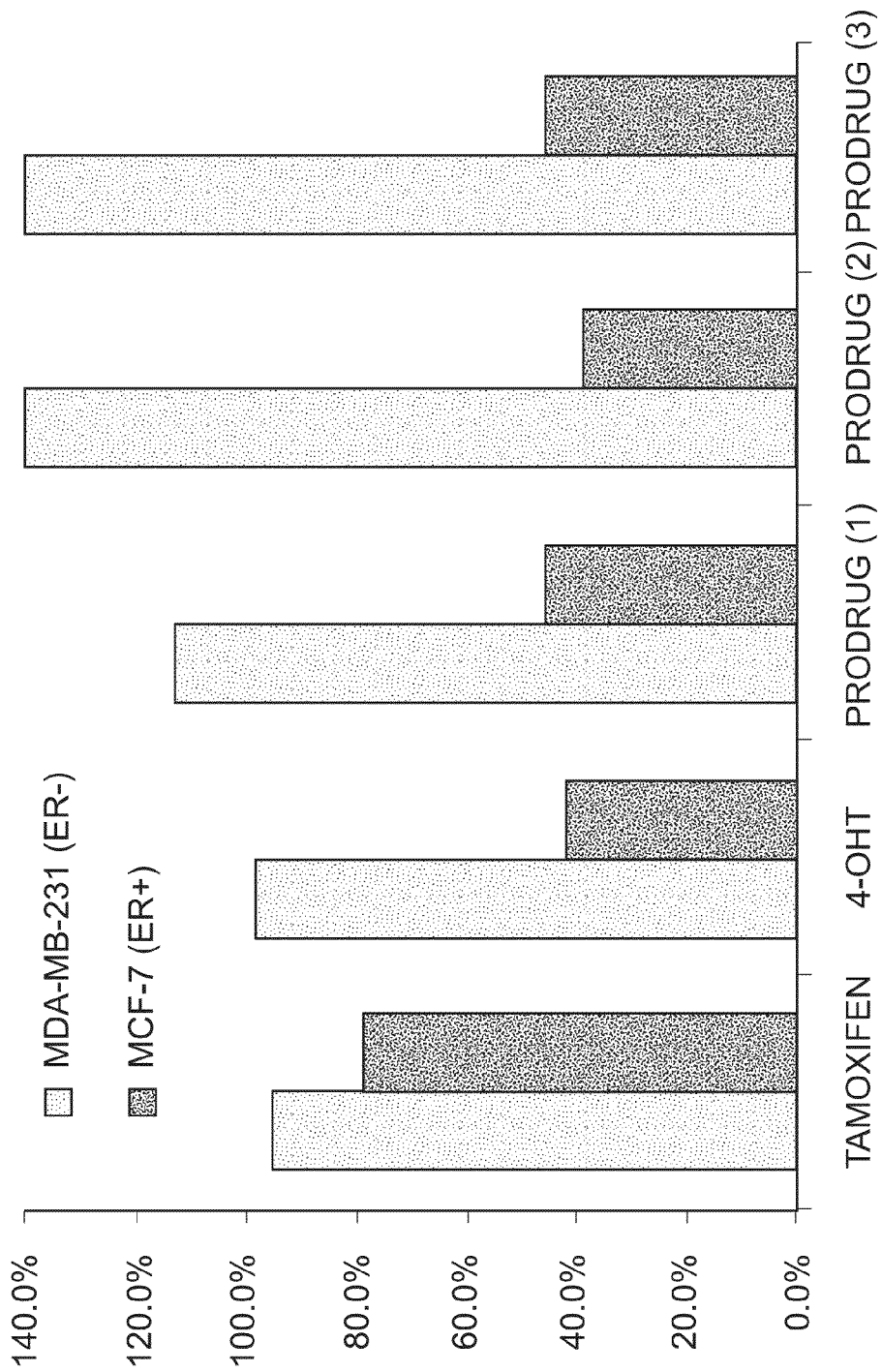

FIG. 9. Effect of Prodrugs 1, 2, and 3 on ER Negative Breast Cancer

FIG. 9 shows the effect of prodrugs on cell growth in ER negative (MDA-MB-231) and ER positive (MCF-7) breast cancer cells.

Figure 10:
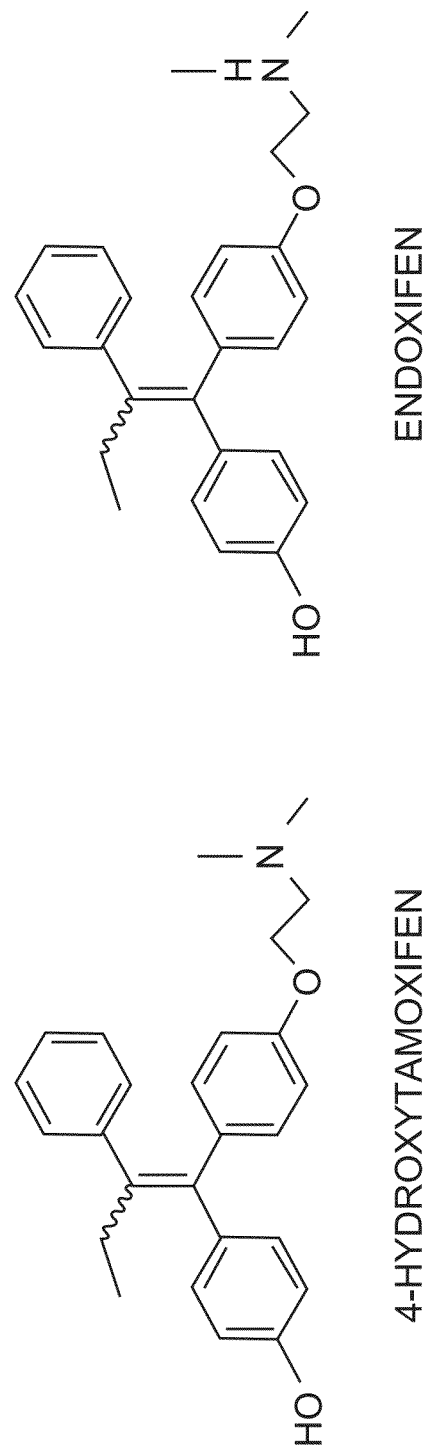

FIG. 10. 4-Hydroxytamoxifen and Endoxifen.

FIG. 10 shows the structure of 4-hydroxytamoxifen and endoxifen.

Figure 11:
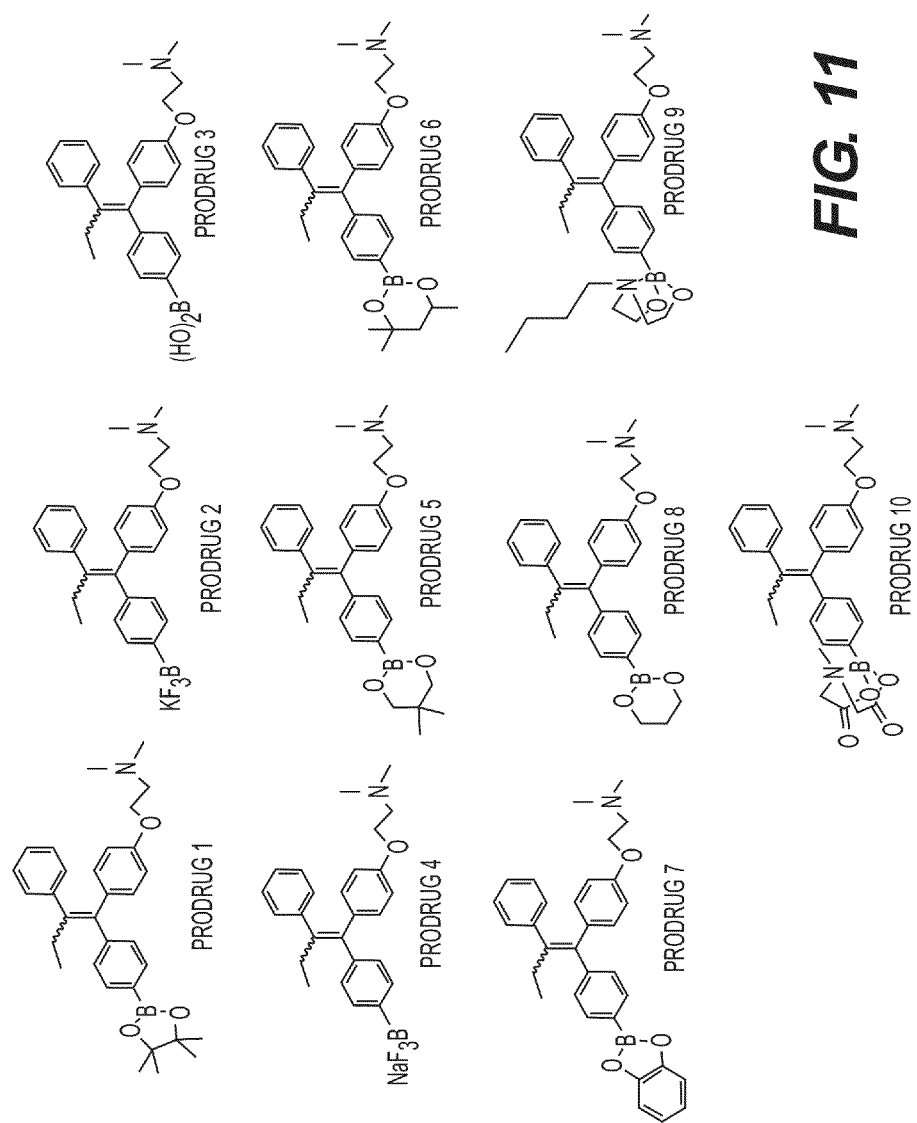

FIG. 11. Boron-Based 4-OHT Prodrugs

FIG. 11 illustrates the structure of prodrugs 1-10, collectively referred to as boron-based 4-OHT prodrugs.

The novel 4-OHT prodrugs 1-10 illustrated in FIG. 11 are defined as follows:

novel 4-OHT prodrug 1: N,N-Dimethyl-2-(4-(2-phenyl-1-(4-(4,4,5,5-tetramethyl-1,3,2-dioxaborolan-2-yl)phenyl)but-1-en-1-yl)phenoxy)ethanamine novel 4-OHT prodrug 2: Potassium (4-(1-(4-(2-(dimethylamino) ethoxy)phenyl)-2-phenylbut-1-en-1-yl)phenyl) trifluoroboronate.

novel 4-OHT prodrug 3: (4-(1-(4-(2-(Dimethylamino) ethoxy)phenyl)-2-phenylbut-1-en-1-yl)phenyl)boronic acid.

novel 4-OHT prodrug 4: Sodium (4-(1-(4-(2-(dimethylamino) ethoxy)phenyl)-2-phenylbut-1-en-1-yl)phenyl) trifluoroboronate.

novel 4-OHT prodrug 5: 2-(4-(1-(4-(5,5-Dimethyl-1,3,2-dioxaborinan-2-yl)phenyl)-2-phenylbut-1-en-1-yl)phenoxy)-N,N-dimethylethanamine.

novel 4-OHT prodrug 6: N,N-Dimethyl-2-(4-(2-phenyl-1-(4-(4,4,6-trimethyl-1,3,2-dioxaborinan-2-yl)phenyl)but-1-en-1-yl)phenoxy)ethanamine.

novel 4-OHT prodrug 7: 2-(4-(1-(4-(Benzo[d][1,3,2]dioxaborol-2-yl)phenyl)-2-phenylbut-1-en-1-yl)phenoxy)-N,N-dimethylethanamine.

novel 4-OHT prodrug 8: 2-(4-(1-(4-(1,3,2-Dioxaborinan-2-yl)phenyl)-2-phenylbut-1-en-1-yl)phenoxy)-N,N-dimethylethanamine.

novel 4-OHT prodrug 9: (4-(1-(4-(2-(Dimethylamino) ethoxy)phenyl)-2-phenylbut-1-en-1-yl)phenyl) N-methyliminodiacetic acid boronate.

novel 4-OHT prodrug 10: (4-(1-(4-(2-(Dimethylamino) ethoxy)phenyl)-2-phenylbut-1-en-1-yl)phenyl) N-butyldiethanol amine boronate.

Figure 12:
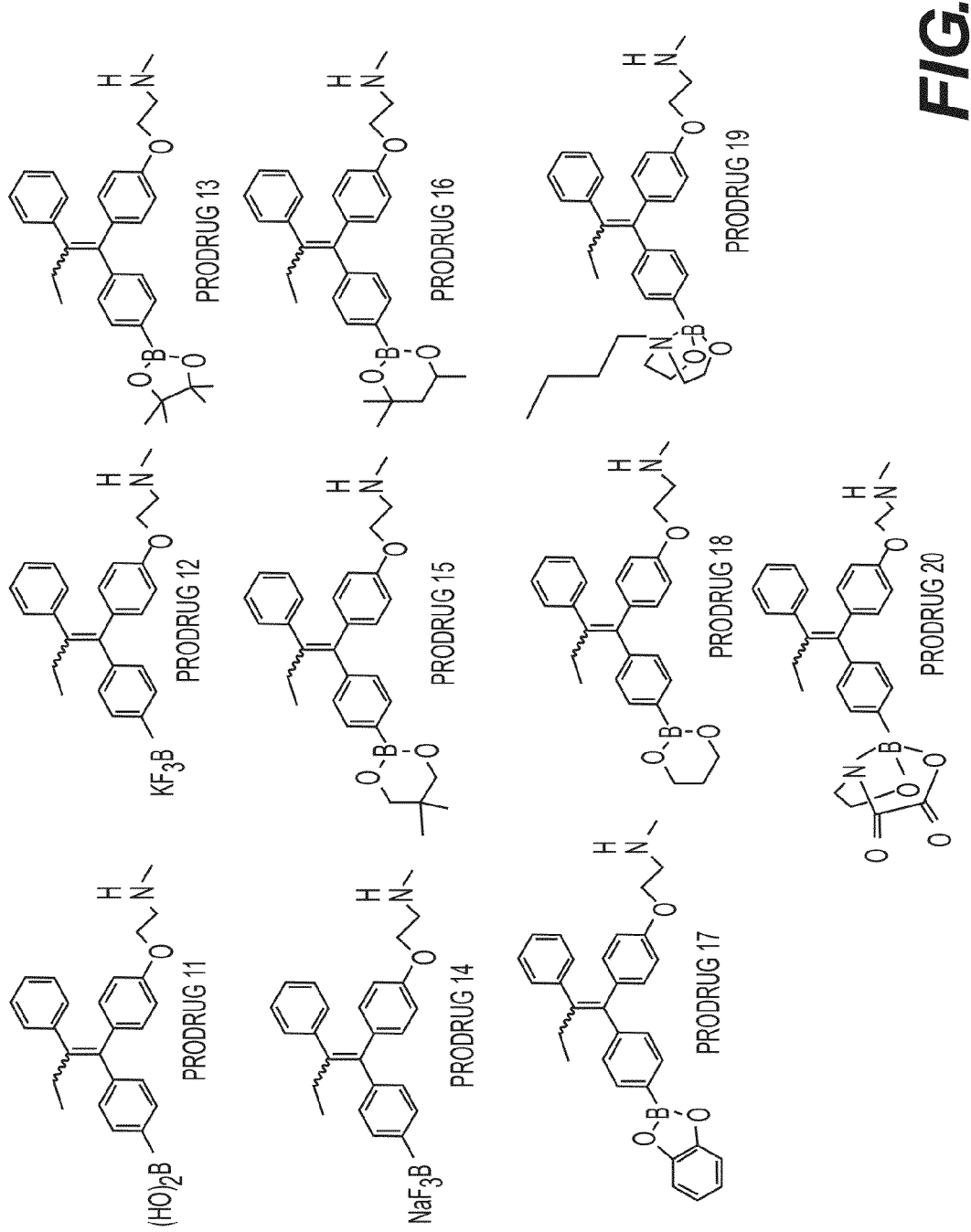

FIG. 12. Boron-Based Endoxifen Prodrugs

FIG. 12 illustrates the structure of prodrugs 11-20, collectively referred to as boron-based endoxifen prodrugs.

The novel endoxifen prodrugs 11-20 illustrated in FIG. 12 are defined as follows:

novel endoxifen prodrug 11, (4-(1-(4-(2-(Methylamino)ethoxy)phenyl)-2-phenylbut-1-en-1-yl)phenyl)boronic acid.

novel endoxifen prodrug 12, Potassium (4-(1-(4-(2-(methylamino) ethoxy)phenyl)-2-phenylbut-1-en-1-yl)phenyl)trifluoroborate.

novel endoxifen prodrug 13, N-Methyl-2-(4-(2-phenyl-1-(4-(4,4,5,5-tetramethyl-1,3,2-dioxaborolan-2-yl)phenyl)but-1-en-1-yl)phenoxy)ethanamine.

novel endoxifen prodrug 14, Sodium (4-(1-(4-(2-(methylamino)ethoxy)phenyl)-2-phenylbut-1-en-1-yl)phenyl)trifluoroboronate.

novel endoxifen prodrug 15, 2-(4-(1-(4-(5,5-Dimethyl-1,3,2-dioxaborinan-2-yl)phenyl)-2-phenylbut-1-en-1-yl)phenoxy)-N-methylethanamine.

novel endoxifen prodrug 16, N-Methyl-2-(4-(2-phenyl-1-(4-(4,4,6-trimethyl-1,3,2-dioxaborinan-2-yl)phenyl)but-1-en-1-yl)phenoxy)ethanamine.

novel endoxifen prodrug 17, 2-(4-(1-(4-(Benzo[d][1,3,2]dioxaborol-2-yl)phenyl)-2-phenylbut-1-en-1-yl)phenoxy)-N-methylethanamine.

novel endoxifen prodrug 18, 2-(4-(1-(4-(1,3,2-Dioxaborinan-2-yl)phenyl)-2-phenylbut-1-en-1-yl)phenoxy)-N-methylethanamine.

novel endoxifen prodrug 19, (4-(1-(4-(2-(Methylamino)ethoxy)phenyl)-2-phenylbut-1-en-1-yl)phenyl)N-methyliminodiacetic acid boronate.

novel endoxifen prodrug 20, (4-(1-(4-(2-(Methylamino)ethoxy)phenyl)-2-phenylbut-1-en-1-yl)phenyl)N-butyldiethanol amine boronate.

Figure 13:
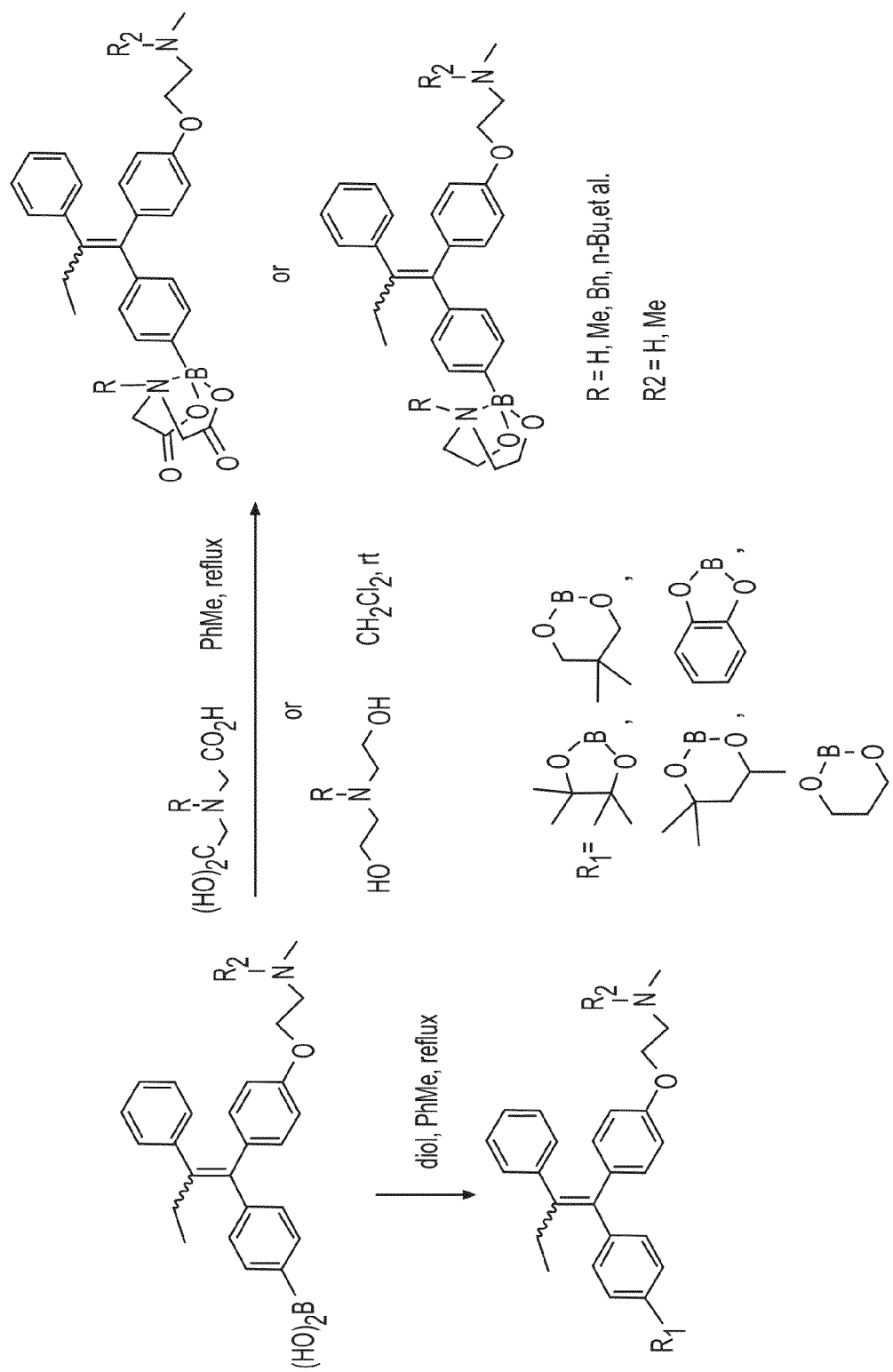

FIG. 13. Synthesis of Boron-4-OHT Prodrugs and Boron-Endoxifen Prodrugs

The synthesis of boron-based 4-OHT prodrugs is outlined in FIG. 13 along with the synthesis of boron-based endoxifen prodrugs.

DETAILED DESCRIPTION

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The disclosure describes the synthesis of novel boron-based 4-hydroxytamoxifen and endoxifen prodrug compounds and their potent anti-proliferation effects on breast cancer cells.

The boron-based 4-hydroxytamoxifen (4-OHT) and endoxifen prodrugs of the present disclosure are compounds of the formula (I):

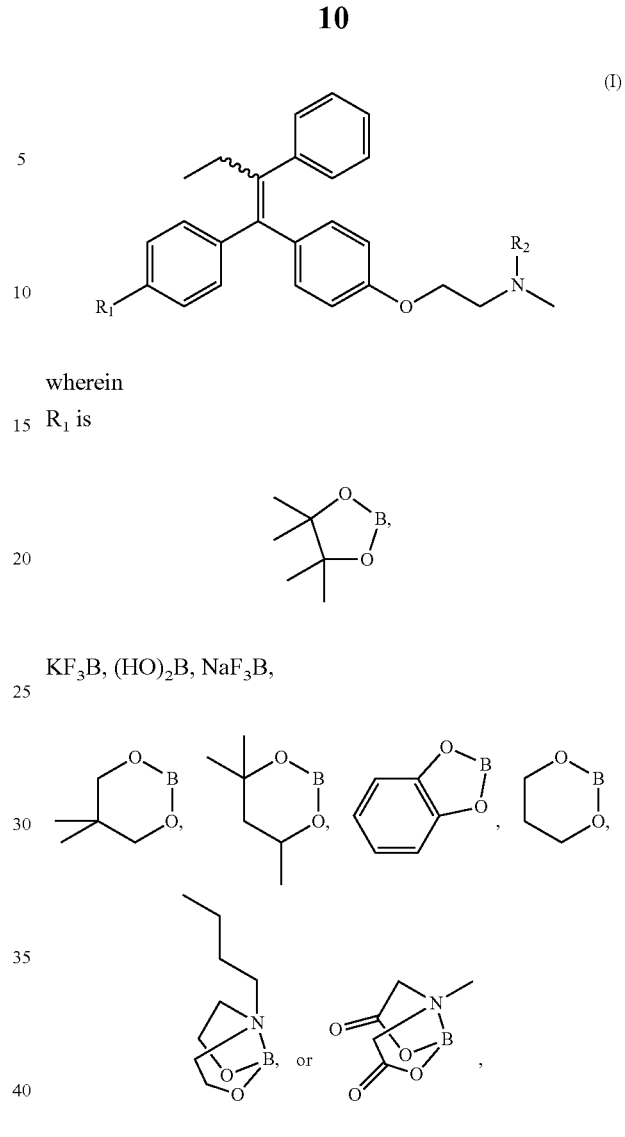

wherein $R_1$ is $KF_3B$, $(HO)_2B$, $NaF_3B$, wherein the $R_1$ substituent point of attachment is on the Boron atom;

and $R_2$ is methyl or hydrogen.

In embodiments in which $R_2$ is methyl, the boron-based prodrugs of formula (I) are collectively termed 4-OHT prodrugs, as illustrated in the chemical structure below:

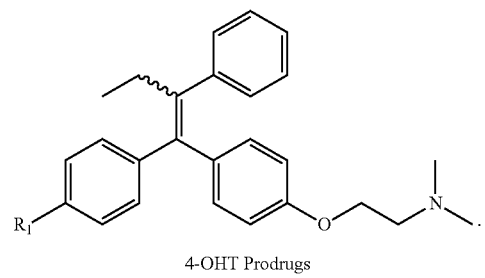

4-OHT Prodrugs

In embodiments in which $R_2$ is hydrogen, the boron-based prodrugs of formula (I) are collectively termed endoxifen prodrugs, as illustrated in the chemical structure below:

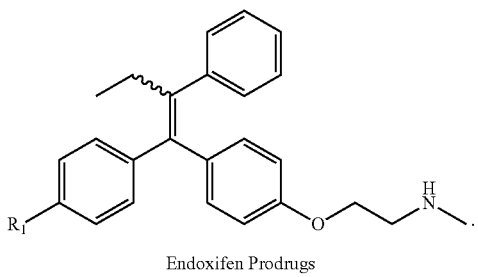

Endoxifen Prodrugs

To determine if the novel boron-based prodrugs have equal or better efficacy than tamoxifen, in vitro breast cancer cell proliferation assays were performed using two estrogen receptor positive cell lines, MCF-7 and T47D.

To determine if the actions of the prodrugs are by means of biotransformation into the compound 4-hydroxytamoxifen, we analyzed the concentrations of the prodrugs and 4-hydroxytamoxifen in the media containing breast cancer cells using an HPLC-MS/MS technique.

Further, tests were performed to determine the efficacy of the novel boron-based prodrugs in an in vivo model.

As used herein, the term "breast cancer" refers to any cancer having its origin in breast (mammary) cells, and includes metastatic and local forms for breast cancer. The terms "minimize" or "reduce", or derivatives thereof, include a complete or partial inhibition of a specified biological effect, which is apparent from the context in which the terms "minimize" or "reduce" are used.

Boronic derivatives of tamoxifen as 4-OHT prodrug candidates were designed by replacing the hydroxyl group with a boron atom that is linked to various functional groups. The parent compounds are described below and in FIG. 10:

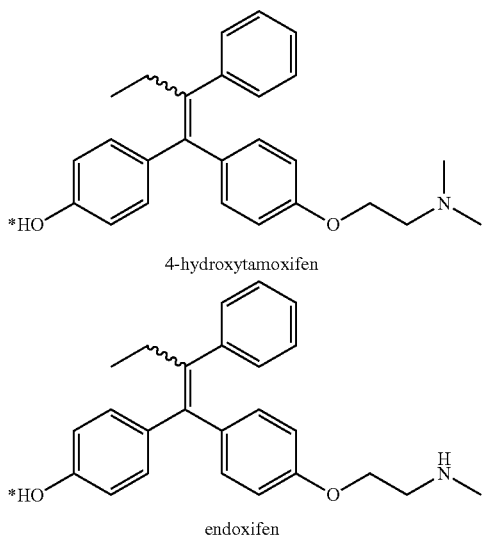

4-hydroxytamoxifen endoxifen

The hydroxyl group that is being replaced with a boron atom, which is linked to various functional groups, is indicated with an (*) in the above chemical structures.

For example, the following chemical structure of prodrug 1 illustrates the point of attachment of the $R_1$ substituent on the Boron atom, which is replacing the hydroxyl group of the parent compounds:

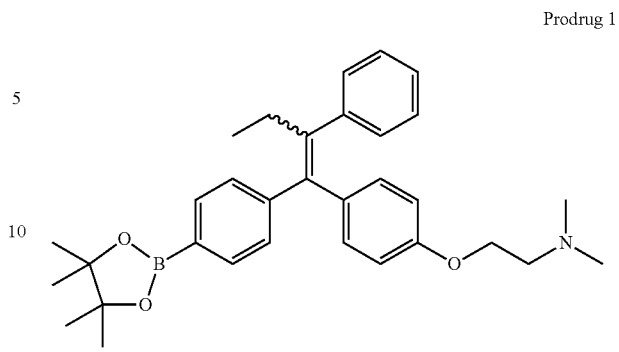

Prodrug 1

The boron-aryl carbon bond may be susceptible to oxidative cleavage by hydrogen peroxide to form a phenolic compound. (see refs. 16-19). Because tumor cells have elevated concentration levels of hydrogen peroxide, (see refs. 20-23) then one possible mechanism of metabolism of the disclosed novel prodrug compounds is that upon entering breast cancer cells, these prodrugs will undergo facile oxidization reaction to form 4-OHT. This is one proposed mechanism relating the novel structure of the boron-based prodrug compounds to that of their function in living organisms.

The below Examples will further illustrate the chemical structure of various embodiments of the novel boron-based prodrug compounds taught herein. Furthermore, the Examples demonstrate the efficacy of various embodiments of the disclosed prodrug compounds. As set forth in the scientific data below, it has been surprisingly found that the disclosed novel boron-based prodrug compounds exhibit superior anti-proliferative efficacy in ER+ MCF-7 and T47D cell lines as compared to tamoxifen.

EXAMPLES

Example 1

Synthesis of Boron-4-Hydroxytamoxifen and Boron-Endoxifen Prodrugs

Prodrug 1 Synthesis

To synthesize N,N-dimethyl-2-(4-(2-phenyl-1-(4-(4,4,5,5-tetramethyl-1,3,2-dioxaborolan-2-yl)phenyl)but-1-en-1-yl)phenoxy)ethanamine (prodrug 1), the following procedure was used: to a 1,4-dioxane solution of the triflate (0.30 g, 0.57 mmol) were added bis(pinacolato)diboron (0.16 g, 0.63 mmol), $PdCl_2(dppf)$ (0.025 g, 5% mol) and KOAc (0.14 g, 1.43 mmol), and the mixture was stirred under $N_2$ at 80° C. overnight. After the solution was cooled, the dioxane was removed under vacuum, and $CH_2Cl_2$ and water were added. The resulting mixture was extracted with dichloromethane twice, and the combined organic layer was washed with brine and then dried over $MgSO_4$. The organic solvent was concentrated in vacuo. The crude product was purified by flash chromatography to afford (1) (0.26 g) in 90% yield. Structural confirmation data was also obtained: $^1$H-NMR ($CDCl_3$): 7.78 (1H, d, J=8.0 Hz), 7.43 (1H, d, J=7.6 Hz), 7.30-7.03 (7H, m), 6.91-6.84 (2H, m), 6.76 (1H, d, J=8.4 Hz), 6.51 (1H, d, J=8.4 Hz), 4.48 (1H, t, J=5.6 Hz), 4.30 (1H, t, J=5.6 Hz), 3.49 (1H, t, J=5.6 Hz), 3.38 (1H, t, J=5.6 Hz), 2.93 (3H, s), 2.85 (3H, s), 2.49-2.39 (2H, m), 1.33 (6H, s), 1.26 (3H, s), 0.92 (3H, m). $^{13}$C-NMR ($CDCl_3$): 156.1, 155.3, 146.8, 146.4, 143.1, 142.4, 142.3, 142.2, 138.1, 138.0, 137.5, 136.9, 134.9, 134.1, 132.6, 132.3, 131.11, 131.08, 130.4, 129.8, 129.7, 129.1, 128.3, 128.2, 128.1, 126.5, 120.4, 114.7, 114.4, 113.6, 84.0, 83.8, 63.2, 63.0, 62.7, 56.9, 56.8, 56.7, 44.1, 44.0, 43.9, 29.3, 25.11, 25.06, 13.8, 13.71, 13.65. ESI (+): 498.25 (M+H). HRMS (ESI(+)): Calcd. for $C_{32}H_{41}BNO_3$ (M+H): 498.3179. Found: 498.3172.

Prodrug 2 Synthesis

To synthesize Potassium (4-(1-(4-(2-(dimethylamino)ethoxy)phenyl)-2-phenylbut-1-en-1-yl)phenyl)trifluoroborate (prodrug 2), the following procedure was used: to a solution of the pinacolylboronate (0.26 g, 0.52 mmol) in methanol was added aqueous potassium bifluoride (0.8 ml, 3M, 2.4 mmol). The resulting mixture was stirred at room temperature for 15 min, concentrated in vacuo and dissolved in hot acetone. The mixture was filtered, the filtrate was concentrated in vacuo and the residue recrystallized from acetone and ether to afford potassium trifluoroborate 2 (0.16 g) in 65% yield as a crystalline solid. Structural confirmation data was also obtained: $^1$H-NMR (CD$_3$CN): 7.46 (2H, d, J=7.2 Hz), 7.23-7.11 (5H, m), 7.06 (2H, d, J=7.6 Hz), 6.93 and 6.85 (2H, d, J=8.8 Hz), 6.72 and 6.60 (2H, d, J=8.8 Hz), 4.17 and 4.02 (2H, t, J=5.2 Hz), 3.16 and 3.08 (2H, t, J=5.2 Hz), 2.65 and 2.59 (6H, s), 2.44 (2H, q, J=7.2 Hz), 0.91 (3H, m). $^{13}$C-NMR (CD$_3$CN): 156.9, 156.1, 143.3, 140.9, 139.6, 137.6, 137.3, 131.9, 131.5, 130.8, 130.6, 130.0, 129.9, 126.2, 115.6, 114.4, 113.6, 63.3, 57.3, 44.2, 29.0, 13.1. ESI (−): 438.25 (M-K). HRMS (ESI(+)): Calcd. for $C_{26}H_{29}BF_3KNO$ (M+H): 478.1931. Found: 478.1944.

Prodrug 3 Synthesis

To synthesize (4-(1-(4-(2-(dimethylamino)ethoxy)phenyl)-2-phenylbut-1-en-1-yl)phenyl) boronic acid (prodrug 3), the following procedures was used: to a solution of the potassium trifluoroborate 2 (0.16 g, 0.33 mmol) in water and acetonitrile was added trimethylsilyl chloride (0.10 g, 1.0 mmol). The resulting solution was stirred at room temperature for 1 h, quenched with saturated sodium bicarbonate, and extracted with dichloromethane. The combined organic solution was dried over MgSO$_4$, filtered and concentrated in vacuo to afford the corresponding boronic acid 3 (0.13 g) in 98% yield as a white solid. Structural confirmation data was also obtained: $^1$H-NMR ((CD$_3$)$_2$CO): 7.90 (1H, d, J=8.0 Hz), 7.54 (1H, d, J=8.0 Hz), 7.27-7.02 (10H, m), 6.89 (1H, d, J=8.0 Hz), 6.84 (1H, d, J=8.8 Hz), 6.67 (1H, d, J=8.8 Hz), 4.52 and 4.34 (2H, t, J=4.8 Hz), 3.84 and 3.74 (2H, t, J=4.8 Hz), 3.20 and 3.13 (6H, s), 2.46 (2H, m), 0.90 (3H, m). $^{13}$C-NMR ((CD$_3$)$_2$CO): 156.0, 145.8, 142.5, 142.4, 141.8, 138.8, 138.7, 136.7, 135.5, 134.4, 133.6, 132.0, 130.7, 130.0, 129.9, 128.6, 128.2, 128.0, 126.4, 114.7, 113.8, 75.8, 62.2, 62.0, 56.9, 43.6, 13.1. ESI (+): 416.25 (M+H). HRMS (ESI(+)): Calcd. for $C_{26}H_{31}BNO_3$ (M+H): 416.2397. Found: 416.2392.

Prodrug 11 Synthesis

To prepare the boronic derivatives of endoxifen (prodrug 11), the following procedure was used:

Step 1: To a 1,4-dioxane solution of the triflate (0.38 g, 0.57 mmol) were added bis(pinacolato)diboron (0.16 g, 0.63 mmol), PdCl$_2$ (dppf) (0.025 g, 5% mol) and KOAC (0.14 g, 1.43 mmol), and the mixture was stirred at 130° C. overnight. After the solution was cooled, filtered on vacuum, diluted with ethyl acetate, washed with brine and dried over MgSO$_4$. Then the solvent was removed on vacuum, and the residue was purified with flash chromatography to afford the pinacol boronic ester product (0.10 g) in 80% yield. $^1$H-NMR (CD$_3$Cl): 7.81 (1H, d, J=8.1 Hz), 7.45 (1H, d, J=8.4 Hz), 7.25~7.12 (7H, m), 6.90~6.85 (2H, m), 6.77 (1H, d, J=8.7 Hz), 6.53 (1H, d, J=8.7 Hz), 4.16~3.97 (4H, m), 3.67~3.56 (2H, m), 3.06 and 2.98 (3H, s), 2.52~2.43 (2H, m), 1.37 (3H, s), 1.29~1.28 (12H, m), 0.98~0.90 (3H, m). $^{13}$C-NMR (CD$_3$Cl): 146.87, 146.40, 142.29, 142.14, 134.61, 133.80, 131.97, 130.71, 130.24, 129.66, 128.91, 127.87, 126.18, 113.98, 113.25, 83.81, 83.72, 83.64, 61.56, 35.99, 29.09, 24.99, 24.89, 24.84, 24.55, 14.68, 13.58. HRMS (ESI(+)): Calcd. for $C_{34}H_{42}BNO_5$ (M+H): 556.3234. Found: 556.3231.

Step 2: To a freshly distilled THF solution (E,Z)-ethyl methyl (2-(4-(2-phenyl-1-(4-(4,4,5,5-tetramethyl-1,3,2-dioxaborolan-2-yl)phenyl)but-1-en-1-yl)phenoxy)ethyl)carbamate (0.10 g, 0.18 mmol) cooled to −78° C. in a dry ice/acetone bath while 0.125 mL of butyllithium solution (1.6M in hexanes, 0.2 mmol) is added dropwise via syringe. After 15 min, the dry ice/acetone bath was removed and the reaction mixture is allowed to warm to room temperature and stirred overnight. The resulting mixture was quenched with saturated NH$_4$Cl solution an extracted with ethyl acetate. And the combined organic layer was washed with brine and then dried over MgSO$_4$. The organic solvent was concentrated in vacuo. The crude was purified by flash chromatography to afford prodrug 11 (0.048 g) in 67% yield. Structural confirmation data was also obtained: $^1$H-NMR (CD$_3$OD): 7.61 (1H, d, J=6.6 Hz), 7.20~7.18 (4H, m), 7.14~7.12 (4H, m), 7.01 (1H, m), 6.83 (2H, d, J=8.7 Hz), 6.66 (2H, d, J=8.7 Hz), 4.28~4.08 (2H, t, J=5.1 Hz), 3.38~3.26 (2H, m), 2.74 and 2.68 (3H, s), 2.51~2.44 (2H, m), 0.95~0.89 (3H, m). $^{13}$C-NMR (CD$_3$OD): 136.38, 133.05, 131.69, 130.35, 129.48, 129.42, 128.03, 127.50, 127.46, 125.75, 113.92, 113.07, 63.69, 63.35, 32.89, 32.77, 28.47, 12.44. HRMS (ESI(+)): Calcd. for $C_{25}H_{29}BNO_3$ (M+H): 402.2240. Found: 402.2239.

The remaining prodrugs disclosed can be synthesized by similar methods, as elaborated upon in FIG. 13.

Prodrug Compound List and Identifications

A listing of prodrug compounds encompassed by the present disclosure and their chemical nomenclature, along with their chemical structure, is found below.

Prodrug 1

N,N-Dimethyl-2-(4-(2-phenyl-1-(4-(4,4,5,5-tetramethyl-1,3,2-dioxaborolan-2-yl)phenyl)but-1-en-1-yl)phenoxy)ethanamine is referred to as compound 1, or prodrug 1, or novel boron-based 4-OHT prodrug 1, and represented by the number 1. The chemical structure of prodrug 1 is as follows:

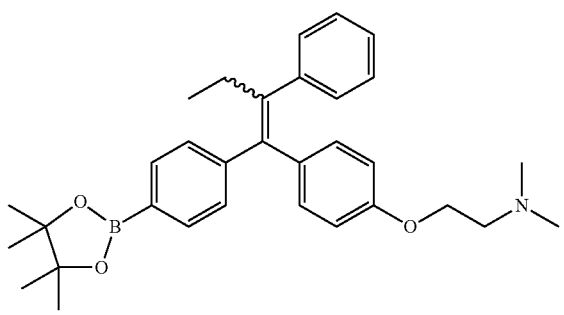

Prodrug 1

Prodrug 2

Potassium (4-(1-(4-(2-(dimethylamino)ethoxy)phenyl)-2-phenylbut-1-en-1-yl)phenyl)trifluoro boronate is referred to as compound 2, or prodrug 2, or novel boron-based 4-OHT prodrug 2, and represented by the number 2. The chemical structure of prodrug 2 is as follows:

Prodrug 2

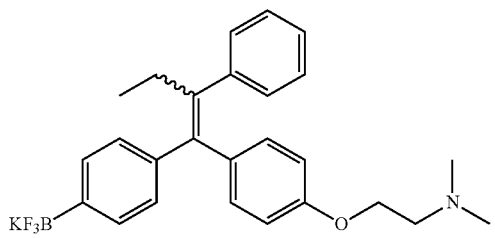

Prodrug 3
(4-(1-(4-(2-(Dimethylamino)ethoxy)phenyl)-2-phenylbut-1-en-1-yl)phenyl)boronic acid is referred to as compound 3, or prodrug 3, or novel boron-based 4-OHT prodrug 3, and represented by the number 3. The chemical structure of prodrug 3 is as follows:

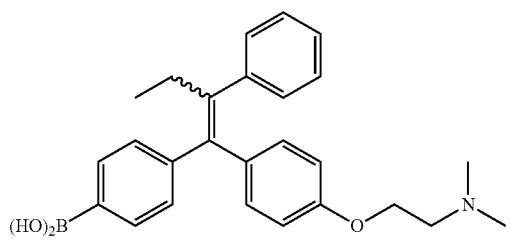

Prodrug 3

Prodrug 4
Sodium (4-(1-(4-(2-(dimethylamino)ethoxy)phenyl)-2-phenylbut-1-en-1-yl)phenyl)trifluoroboronate is referred to as compound 4, or prodrug 4, or novel boron-based 4-OHT prodrug 4, and represented by the number 4. The chemical structure of prodrug 4 is as follows:

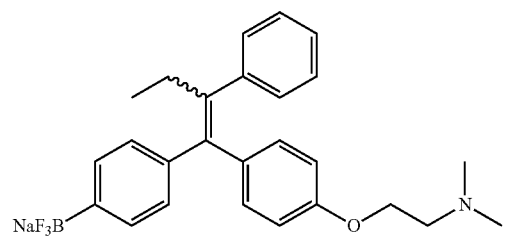

Prodrug 4

Prodrug 5
2-(4-(1-(4-(5,5-Dimethyl-1,3,2-dioxaborinan-2-yl)phenyl)-2-phenylbut-1-en-1-yl)phenoxy)-N,N-dimethylethanamine is referred to as compound 5, or prodrug 5, or novel boron-based 4-OHT prodrug 5, and represented by the number 5. The chemical structure of prodrug 5 is as follows:

Prodrug 5

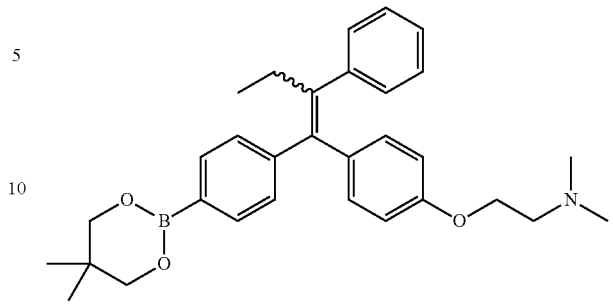

Prodrug 6
N,N-Dimethyl-2-(4-(2-phenyl-1-(4-(4,4,6-trimethyl-1,3,2-dioxaborinan-2-yl)phenyl)but-1-en-1-yl)phenoxy)ethanamine is referred to as compound 6, or prodrug 6, or novel boron-based 4-OHT prodrug 6, and represented by the number 6. The chemical structure of prodrug 6 is as follows:

Prodrug 6

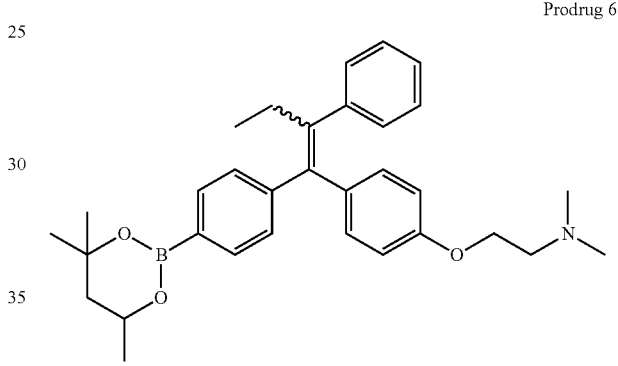

Prodrug 7
2-(4-(1-(4-(Benzo[d][1,3,2]dioxaborol-2-yl)phenyl)-2-phenylbut-1-en-1-yl)phenoxy)-N,N-dimethylethanamine is referred to as compound 7, or prodrug 17, or novel boron-based 4-OHT prodrug 7, and represented by the number 7. The chemical structure of prodrug 7 is as follows:

Prodrug 7

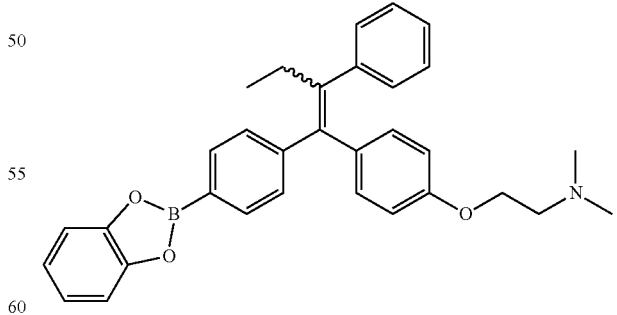

Prodrug 8
2-(4-(1-(4-(1,3,2-Dioxaborinan-2-yl)phenyl)-2-phenylbut-1-en-1-yl)phenoxy)-N,N-dimethylethanamine is referred to as compound 8, or prodrug 8, or novel boron-based 4-OHT prodrug 8, and represented by the number 8. The chemical structure of prodrug 8 is as follows:

Prodrug 8

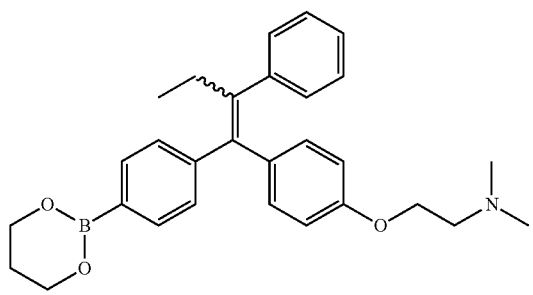

Prodrug 9

Prodrug 9

(4-(1-(4-(2-(Dimethylamino)ethoxy)phenyl)-2-phenyl-but-1-en-1-yl)phenyl)N-methyliminodiacetic acid boronate is referred to as compound 9, or prodrug 9, or novel boron-based 4-OHT prodrug 9, and represented by the number 9. The chemical structure of prodrug 9 is as follows:

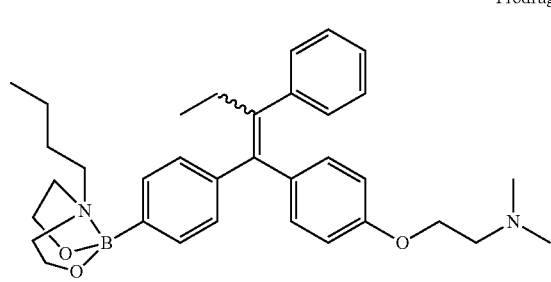

Prodrug 10

Prodrug 10

(4-(1-(4-(2-(Dimethylamino)ethoxy)phenyl)-2-phenyl-but-1-en-1-yl)phenyl)N-butyldiethanol amine boronate is referred to as compound 10, or prodrug 10, or novel boron-based 4-OHT prodrug 10, and represented by the number 10. The chemical structure of prodrug 10 is as follows:

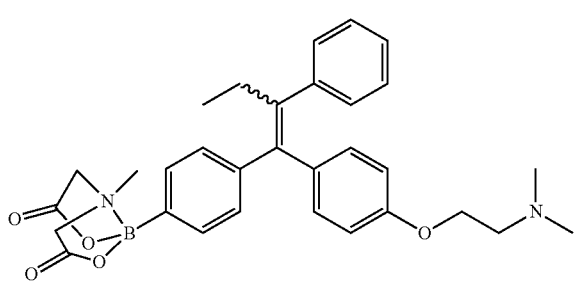

Prodrug 11

Prodrug 11

(4-(1-(4-(2-(Methylamino)ethoxy)phenyl)-2-phenylbut-1-en-1-yl)phenyl)boronic acid is referred to as compound 11, or prodrug 11, or novel boron-based endoxifen prodrug 11, and represented by the number 11. The chemical structure of prodrug 11 is as follows:

Prodrug 11

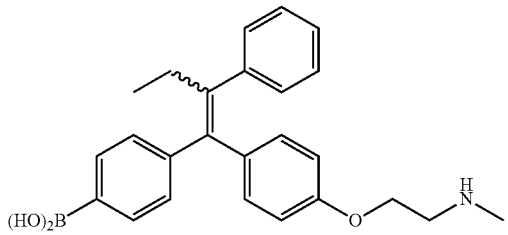

Prodrug 12

Potassium (4-(1-(4-(2-(methylamino)ethoxy)phenyl)-2-phenylbut-1-en-1-yl)phenyl)trifluoroborate is referred to as compound 12, or prodrug 12, or novel boron-based endoxifen prodrug 12, and represented by the number 12. The chemical structure of prodrug 12 is as follows:

Prodrug 12

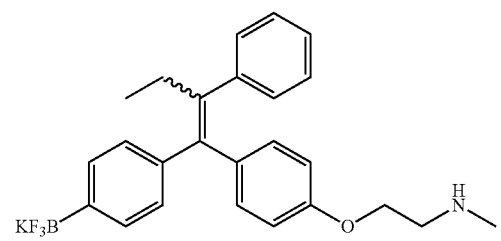

Prodrug 13

N-Methyl-2-(4-(2-phenyl-1-(4-(4,4,5,5-tetramethyl-1,3,2-dioxaborolan-2-yl)phenyl)but-1-en-1-yl)phenoxy)ethanamine is referred to as compound 13, or prodrug 13, or novel boron-based endoxifen prodrug 13, and represented by the number 13. The chemical structure of prodrug 13 is as follows:

Prodrug 13

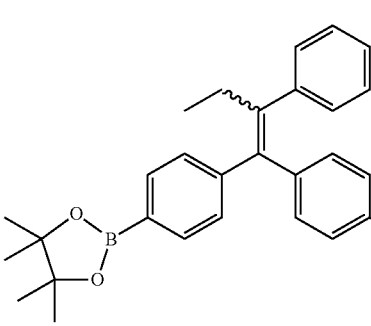

Prodrug 14

Sodium (4-(1-(4-(2-(methylamino)ethoxy)phenyl)-2-phenylbut-1-en-1-yl)phenyl)trifluoroboronate is referred to as compound 14, or prodrug 14, or novel boron-based endoxifen prodrug 14, and represented by the number 14. The chemical structure of prodrug 14 is as follows:

Prodrug 14

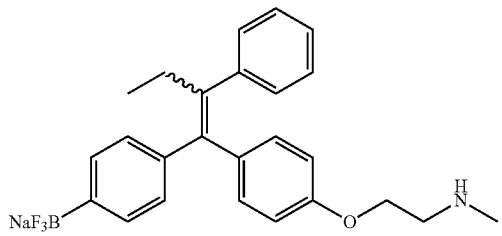

Prodrug 15

2-(4-(1-(4-(5,5-Dimethyl-1,3,2-dioxaborinan-2-yl)phenyl)-2-phenylbut-1-en-1-yl)phenoxy)-N-methylethanamine is referred to as compound 15, or prodrug 15, or novel boron-based endoxifen prodrug 15, and represented by the number 15. The chemical structure of prodrug 15 is as follows:

Prodrug 15

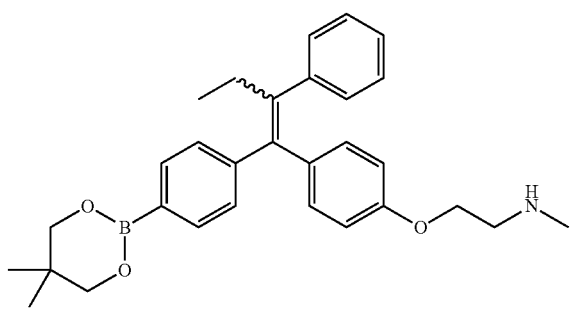

Prodrug 16

N-Methyl-2-(4-(2-phenyl-1-(4-(4,4,6-trimethyl-1,3,2-dioxaborinan-2-yl)phenyl)but-1-en-1-yl)phenoxy)ethanamine is referred to as compound 16, or prodrug 16, or novel boron-based endoxifen prodrug 16, and represented by the number 16. The chemical structure of prodrug 16 is as follows:

Prodrug 16

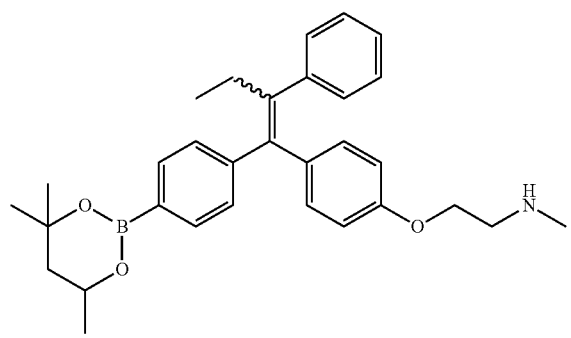

Prodrug 17

2-(4-(1-(4-(Benzo[d][1,3,2]dioxaborol-2-yl)phenyl)-2-phenylbut-1-en-1-yl)phenoxy)-N-methylethanamine is referred to as compound 17, or prodrug 17, or novel boron-based endoxifen prodrug 17, and represented by the number 17. The chemical structure of prodrug 17 is as follows:

Prodrug 17

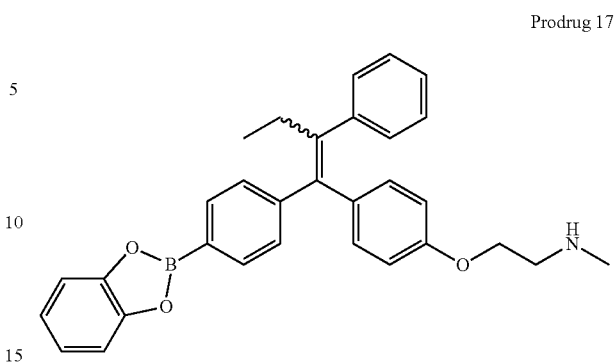

Prodrug 18

2-(4-(1-(4-(1,3,2-Dioxaborinan-2-yl)phenyl)-2-phenylbut-1-en-1-yl)phenoxy)-N-methylethanamine is referred to as compound 18, or prodrug 18, or novel boron-based endoxifen prodrug 18, and represented by the number 18. The chemical structure of prodrug 18 is as follows:

Prodrug 18

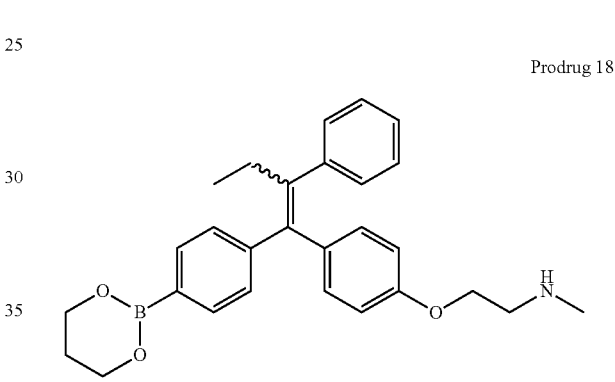

Prodrug 19

(4-(1-(4-(2-(Methylamino)ethoxy)phenyl)-2-phenylbut-1-en-1-yl)phenyl)N-methyliminodiacetic acid boronate is referred to as compound 19, or prodrug 19, or novel boron-based endoxifen prodrug 19, and represented by the number 19. The chemical structure of prodrug 19 is as follows:

Prodrug 19

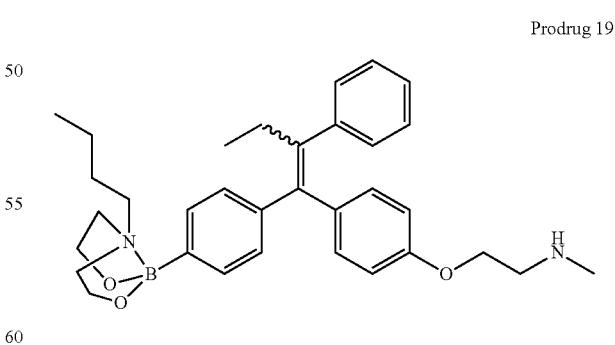

Prodrug 20

(4-(1-(4-(2-(Methylamino)ethoxy)phenyl)-2-phenylbut-1-en-1-yl)phenyl)N-butyldiethanol amine boronate is referred to as compound 20, or prodrug 20, or novel boron-based endoxifen prodrug 20, and represented by the number 20. The chemical structure of prodrug 20 is as follows:

Prodrug 20

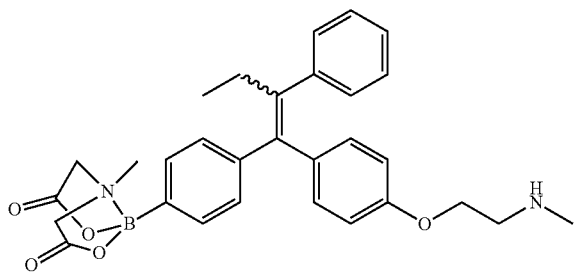

The prodrug compounds 1-10 are referred to collectively as boron-based 4-OHT prodrugs, while the prodrug compounds 11-20 are referred to collectively as boron-based endoxifen prodrugs.

Example 2

Boron Prodrugs Inhibit Survival and Growth of ER+ MCF-7 and T47D Cells

To test if the prodrugs inhibit breast cancer cell growth and proliferation, cell survival assays were conducted. As shown in FIG. 3, Tamoxifen inhibited MCF-7 cell survival and growth by 18% and 52% at $10^{-7}$ M and $10^{-6}$ M, respectively. In comparison, prodrug 1 showed 52% growth inhibition at $10^{-7}$ M and 63% at $10^{-6}$ M. The prodrug 2 demonstrated growth inhibition on MCF-7 cells by 59% at $10^{-7}$ M and 76% inhibition at $10^{-6}$ M concentration. Prodrug 3 inhibited cell growth with comparable efficacies at the two doses, with a 51% inhibition at $10^{-7}$ M and 75% inhibition at $10^{-6}$ M. The endoxifen prodrug 11 also exhibited greater anti-proliferative efficacy than tamoxifen.

To test if the prodrugs can inhibit growth in another breast cancer cell line that also expresses the estrogen receptor, T47D cells were used. Survival assays using T47D cells confirmed the efficacies of the prodrugs (FIG. 4). The prodrugs were equally effective in T47D cells compared to Tamoxifen at $10^{-7}$ M and their overall potency was slightly higher than Tamoxifen at $10^{-6}$ M. For example, the prodrug 1 achieved 60% growth inhibitions of the T47D cells at $10^{-6}$ M, compared to 46% inhibition by Tamoxifen at $10^{-6}$ M. The treatment of T47D cells with prodrugs 2 and 3 at $10^{-6}$ M resulted in 50% and 54% inhibition, respectively. The boron-endoxifen prodrug (11) demonstrated 40% inhibition at $10^{-7}$ M and 53% inhibition at $10^{-6}$ M.

Example 3

$IC_{50}$ Values of the Derived Prodrugs 1, 2, 3, and 11 Compared to Tamoxifen

Tests were undertaken to evaluate the $IC_{50}$ values of the derived prodrugs 1, 2, 3, and 11 compared to the $IC_{50}$ value of tamoxifen.

Table 1 shows the $IC_{50}$ values of the prodrugs obtained from dose-response studies performed to evaluate the antiestrogenic effects of the prodrugs on MCF-7 and T47D cells, as compared with tamoxifen and 4-OHT. A dose-response curve for each drug was obtained yielding $IC_{50}$ values as listed in Table 1.

The $IC_{50}$ concentration of tamoxifen in MCF-7 and T47D cells was observed at 0.794 and 1.13 μM, respectively.

In comparison, the novel boron-based prodrug 1 exhibited an $IC_{50}$ concentration of 0.15 μM, which is about 5 times lower than tamoxifen.

The other two novel boron-based 4-OHT prodrugs, 2 and 3, had $IC_{50}$ values of 0.0063 and 0.042 μM, respectively, which is significantly more potent than tamoxifen.

The boron-based endoxifen prodrug (11), also demonstrated greater potency than tamoxifen in both cell lines, with a 0.0255 μM value in MCF-7 cells and a 0.189 μM value in T47D cells.

Thus, the novel boron-based 4-OHT prodrugs 1, 2, and 3, as well as the novel boron-based endoxifen prodrug 11, all demonstrated lower $IC_{50}$ concentrations than tamoxifen in both the MCF-7 and T47D cell lines.

TABLE 1

| | $IC_{50}$ (μM) | |
|---|---|---|
| Drug | MCF-7 | T47D |
| Tamoxifen | 0.794 | 1.13 |
| Boron-4-OHT Prodrug (1) | 0.148 | 0.144 |
| Boron-4-OHT Prodrug (2) | 0.00626 | 0.260 |
| Boron-4-OHT Prodrug (3) | 0.0420 | 0.228 |
| Boron-endoxifen Prodrug (11) | 0.0255 | 0.189 |

Example 4

Boron Prodrugs Underwent Facile Oxidative Cleavage of the Boron Carbon Bond to Yield 4-Hydroxytamoxifen in ER+ MCF-7 and T47D Cells To determine if the prodrugs undergo oxidative cleavage, by intracellular hydrogen peroxide present at elevated concentration levels in the breast cancer cells, the cell culture media was analyzed for concentrations of the prodrugs and the active form of tamoxifen, 4-OHT. Using HPLC coupled to a linear trap mass spectrometer, the prodrugs and their active product, 4-OHT were separated, identified, and quantified.

As shown in the total ion chromatogram (TIC) in FIG. 5, the boronic acid prodrug of 4-OHT (3), was observed at 17.3 min, while the desired active drug form, 4-OHT eluted at 17.6 min. The relative peak areas were measured at 30.4% for prodrug 3 and 69.6% for 4-OHT (FIG. 5 panel A). This result indicates that the majority of the prodrug has been converted to 4-OHT in the media after incubation with MCF-7 cells. This transformation was more complete in T47D cells, where the % peak area of 4-OHT reached 79.1% vs. 20.9% for the prodrug 3 (FIG. 5 panel B).

For prodrugs 1 and 2, the % peak areas of 4-OHT were 73.3% and 81.6%, respectively, in MCF-7 cells (FIG. 5 panel A). Similar results were observed when T47D cells were treated with prodrugs 1 and 2, where 69.9% of prodrug 1 and 86.3% of prodrug 2 were transformed into 4-OHT (FIG. 5 panel B).

Example 5

Boron Prodrugs were Efficacious in a Mouse Xenograft Model

Experiments were conducted to evaluate the anti-estrogenic effects of prodrug 1 on MCF-7 cell tumorigenesis in vivo.

The protocol utilized 4-6 week old ovariectomized female Nu/Nu mice that were injected bilaterally in the mammary fat pad (MFP) with 5×10$^6$ MCF-7 cells in matrigel (reduced factor). All animals were implanted with a 17β-estradiol pellet (0.72 mg, 60-day release) subcutaneously in the lateral area of the neck at the time of cell injection. Tumors were allowed to form and at day 15 post cell injection mice were randomized into groups (n=5). Animals were treated daily with i.p. injections of either vehicle (1:5 DMSO/PBS), Tamoxifen, 4-hydroxytomoxifen, or prodrug 1 (5 mg/kg/animal). Tumor size was measured 3 times weekly using digital calipers.

As FIG. 6 illustrates, at an i.p injection dose of 5 mg/kg/animal, tumor-bearing mice showed significantly smaller tumor sizes at day 38 post MCF-7 cell injection compared to the tumors in untreated mice. These results therefore indicate the applicability of the novel boron-based prodrugs in an in vivo model.

Example 6

Boron Prodrugs Exhibit Increased Uptake by ER+ MCF-7 and T47D Cells

The modification of 4-OHT structure by incorporation of the boron-carbon bond is likely responsible for improved cellular uptake of the disclosed novel prodrugs.

To compare the relative uptake of the prodrugs vs. 4-OHT, experiments were conducted that measured the concentrations of the remaining drugs in media after a 6-day period of incubation with MCF-7 cells.

Results in FIG. 7 show that the concentration of 4-OHT in media is approximately 2-4 times higher than those of prodrugs 1, 2, and 3.

While it is possible that the disclosed novel boron-based prodrugs may have their own antiestrogenic activities, the experimental data suggests that the prodrugs were more efficiently taken up by the cancer cells.

Example 7

Boron Prodrugs Show Desirable Half-Life in ER+ MCF-7 and T47D Cells

A kinetic study on the stability of the prodrugs was performed. In the study, the relative concentration of a prodrug to 4-OHT was determined at different time points that ranged from 0 hour to 144 hours (6 days). Regression of changes of the prodrug (3) concentration relative to that of 4-OHT over time yielded a half-life value of 96 hrs, or 4 days, for prodrug (3). This result is illustrated in FIG. 8.

Similar half-life data were obtained for prodrug (1) (89 hrs) and prodrug (2) (84 hrs).

Example 8

Boron Prodrugs Demonstrate No Apparent Activity in ER− Breast Cancer Cells

An ER negative breast cancer cell line, MDA-MB-231, was used to test the effects of the boron-based prodrugs on cell proliferation. Survival ratios were determined in both the ER− and ER+ cells for comparison.

The boron-based prodrugs did not show any inhibition of cell growth in MDA-MB-231, as evidenced by FIG. 9.

These results confirm that the mechanism of action of the boron-based prodrugs involves ER, as the prodrugs underwent oxidative cleavage of the boron-carbon bond to yield 4-OHT.

Accordingly, the novel boron-based prodrugs of the present disclosure can be provided in vivo to a mammal in need thereof in any manner that is used for tamoxifen. The boron-based prodrugs of the present disclosure can be provided by any route acceptable for administration of tamoxifen, and at any dose acceptable for tamoxifen. For example, the boron-based prodrugs of the present disclosure can be provided at 1 mg, 5 mg, 10 mg, 20 mg, 30 mg, and 40 mg per day.

Thus, the present disclosure provides novel boron-based 4-hydroxytamoxifen (4-OHT) and endoxifen prodrugs that have been discovered to have potent inhibitory effects on cell-proliferation of breast cancer cells that are estrogen receptor positive (ER+). This discovery, and the disclosure of the present boron-based prodrug compounds, addresses a great need in the art for desirable alternatives to tamoxifen for breast cancer patients lacking the active form of the cytochrome P450 2D6 enzyme (CYP2D6).

REFERENCES CITED

1. Harvey, J. M.; Clark, G. M.; Osborne, C. K.; Allred, D. C., Estrogen Receptor Status by Immunohistochemistry Is Superior to the Ligand-Binding Assay for Predicting Response to Adjuvant Endocrine Therapy in Breast Cancer. J. Clin. Oncol. 1999, 17, 1474.
2. Musgrove, E. A.; Sutherland, R. L., Biological Determinants of Endocrine Resistance in Breast Cancer. Nat. Rev. Cancer 2009, 9, 631-643.
3. Hoskins, J. M.; Carey, L. A.; McLeod, H. L., CYP2D6 and Tamoxifen: DNA Matters in Breast Cancer. Nat. Rev. Cancer 2009, 9, 576-586.
4. Bijl, M.; van Schaik, R.; Lammers, L.; Hofman, A.; Vulto, A.; van Gelder, T.; Stricker, B.; Visser, L., The CYP2D6*4 Polymorphism Affects Breast Cancer Survival in Tamoxifen Users. Breast Cancer Res. Treat. 2009, 118, 125-130.
5. Jordan, V. C.; Collins, M. M.; Rowsby, L.; Prestwich, G., A Monohydroxylated Metabolite of Tamoxifen with Potent Antiestrogenic Activity. J. Endocrinol. 1977, 75, 305-316.
6. Jordan, V. C., Metabolites of Tamoxifen in Animals and Man: Identification, Pharmacology, and Significance. Breast Cancer Res. Treat. 1982, 2, 123-138.
7. Robertson, D. W.; Katzenellenbogen, J. A.; Long, D. J.; Rorke, E. A.; Katzenellenbogen, B. S., Tamoxifen Antiestrogens. A Comparison of the Activity, Pharmacokinetics, and Metabolic Activation of the cis and trans Isomers of Tamoxifen. J. Steroid Biochem. 1982, 16, 1-13.
8. Coezy, E.; Borgna, J.-L.; Rochefort, H., Tamoxifen and Metabolites in MCF7 Cells: Correlation between Binding to Estrogen Receptor and Inhibition of Cell Growth. Cancer Res. 1982, 42, 317-323.
9. Furr, B. J. A.; Jordan, V. C., The pharmacology and clinical uses of tamoxifen. Pharmacol. Ther. 1984, 25, 127-205.
10. Desta, Z.; Ward, B. A.; Soukhova, N. V.; Flockhart, D. A., Comprehensive Evaluation of Tamoxifen Sequential Biotransformation by the Human Cytochrome P450 System in Vitro: Prominent Roles for CYP3A and CYP2D6. J. Pharmacol. Exp. Ther. 2004, 310, 1062-1075.
11. Pujol, H.; Girault, J.; Rouanet, P.; Fournier, S.; Grenier, J.; Simony, J.; Fourtillan, J.-B.; Pujol, J.-L., Phase I Study of Percutaneous 4-Hydroxy-tamoxifen with Analyses of 4-Hydroxy-tamoxifen Concentrations in Breast Cancer and Normal Breast Tissue. Cancer Chemother. Pharmacol. 1995, 36, 493-498.
12. Rouanet, P.; Linares-Cruz, G.; Dravet, F.; Poujol, S.; Gourgou, S.; Simony-Lafontaine, J.; Grenier, J.; Kramar, A.; Girault, J.; Le Nestour, E.; Maudelonde, T., Neoadjuvant Percutaneous 4-Hydroxytamoxifen Decreases Breast Tumoral Cell Proliferation: A Prospective Controlled Randomized Study Comparing Three Doses of 4-Hydroxytamoxifen Gel to Oral Tamoxifen. J. Clin. Oncol. 2005, 23, 2980-2987.

13. Mansel, R.; Goyal, A.; Nestour, E.; Masini-Etévé, V.; O'Connell, K., A Phase II Trial of Afimoxifene (4-hydroxytamoxifen gel) for Cyclical Mastalgia in Premenopausal Women. Breast Cancer Res. Treat. 2007, 106, 389-397.

14. Wu, X.; Hawse, J. R.; Subramaniam, M.; Goetz, M. P.; Ingle, J. N.; Spelsberg, T. C., The Tamoxifen Metabolite, Endoxifen, Is a Potent Antiestrogen that Targets Estrogen Receptor afor Degradation in Breast Cancer Cells. Cancer Res. 2009, 69, 1722-1727.

15. Ahmad, A.; Ali, S.; Ahmad, M.; Sheikh, S.; Ahmad, I., Orally Administered Endoxifen is a New Therapeutic Agent for Breast Cancer. Breast Cancer Res. Treat. 2010, 122, 579-584.

16. Ainley, A. D.; Challenger, F., Studies of the Boron-carbon Linkage. Part I. The Oxidation and Nitration of Phenylboric Acid. J. Chem. Soc. 1930, 2171-2180.

17. Kuivila, H. G.; Armour, A. G., Electrophilic Displacement Reactions. IX. Effects of Substituents on Rates of Reactions between Hydrogen Peroxide and Benzeneboronic Acid. J. Amer. Chem. Soc. 1957, 79, 5659-5662.

18. Chang, M. C.; Pralle, A.; Isacoff, E. Y.; Chang, C. J., A selective, cell-permeable optical probe for hydrogen peroxide in living cells. J Am Chem Soc 2004, 126, 15392-3.

19. Du, L.; Li, M.; Zheng, S.; Wang, B., Rational Design of a Fluorescent Hydrogen Peroxide Probe Based on the Umbelliferone Fluorophore. Tetrahedron Lett. 2008, 49, 3045-3048.

20. (Szatrowski, T. P.; Nathan, C. F., Production of Large Amounts of Hydrogen Peroxide by Human Tumor Cells. Cancer Res. 1991, 51, 794-798.

21. Zieba, M.; Suwalski, M.; Kwiatkowska, S.; Piasecka, G.; Grzelewska-Rzymowska, I.; Stolarek, R.; Nowak, D., Comparison of Hydrogen Peroxide Generation and the Content of Lipid Peroxidation Products in Lung Cancer Tissue and Pulmonary Parenchyma. Respir. Med. 2000, 94, 800-805.

22. Lim, S. D.; Sun, C.; Lambeth, J. D.; Marshall, F.; Amin, M.; Chung, L.; Petros, J. A.; Arnold, R. S., Increased Nox1 and Hydrogen Peroxide in Prostate Cancer. Prostate 2005, 62, 200-207.

23. Miguel, L.-L., Dual Role of Hydrogen Peroxide in Cancer: Possible Relevance to Cancer Chemoprevention and Therapy. Cancer Lett. 2007, 252, 1-8.

What is claimed is:
1. A compound of Formula (I):

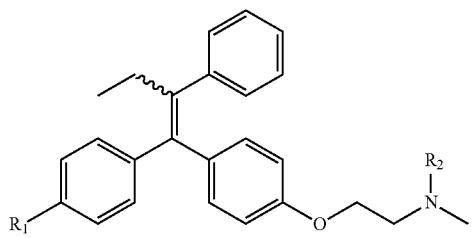

wherein
$R_1$ is

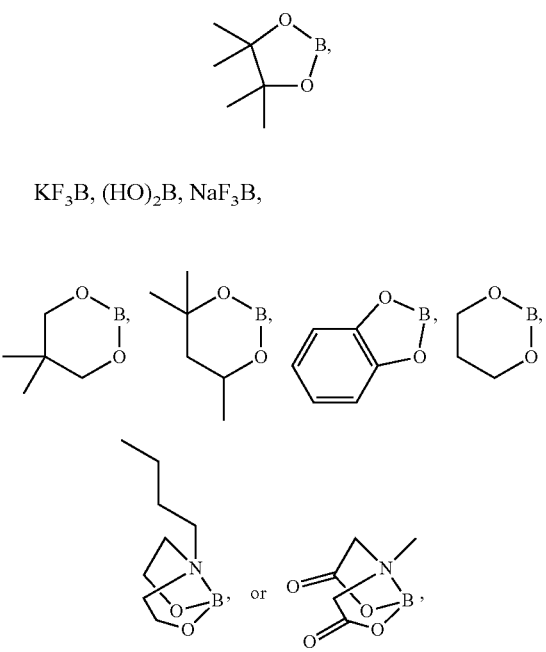

wherein the $R_1$ substituent point of attachment is on the Boron atom;
and
$R_2$ is methyl or hydrogen.

2. A compound according to claim 1, wherein $R_2$ is methyl.

3. A compound according to claim 1, wherein $R_2$ is hydrogen.

4. A compound according to claim 1 selected from the group consisting of

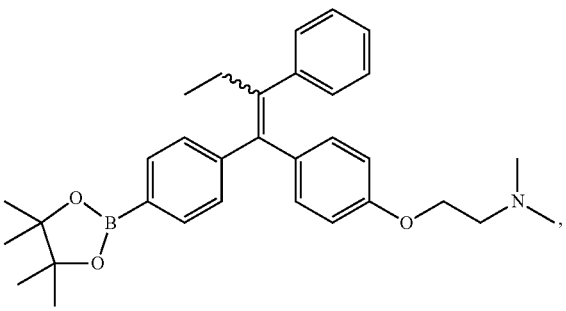

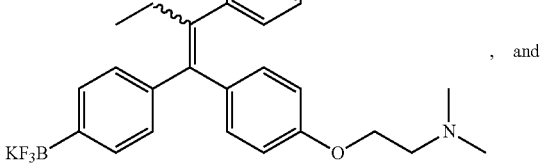

-continued

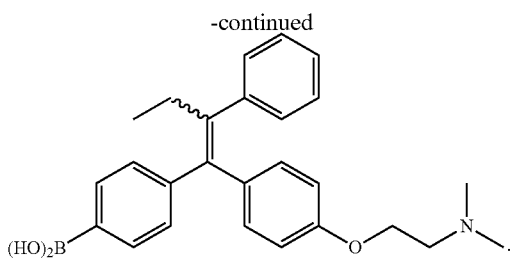

5. A compound according to claim 1 comprising the following structure

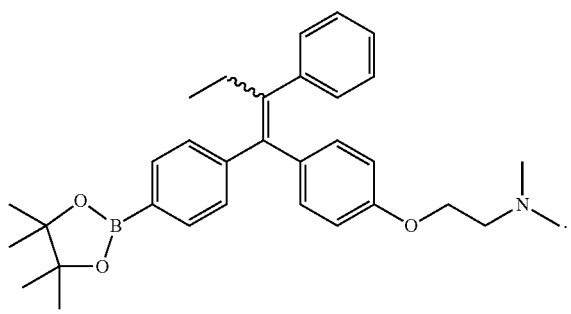

6. A compound according to claim 1 comprising the following structure

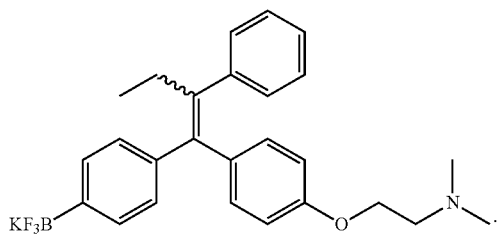

7. A compound according to claim 1 comprising the following structure

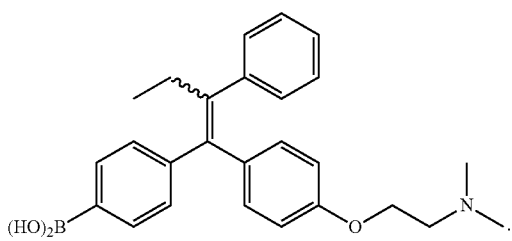 [SMILES: CCC(=C(c1ccc(OCCN(C)C)cc1)c1ccc(B(O)O)cc1)c1ccccc1]

8. A compound according to claim 1 comprising the following structure

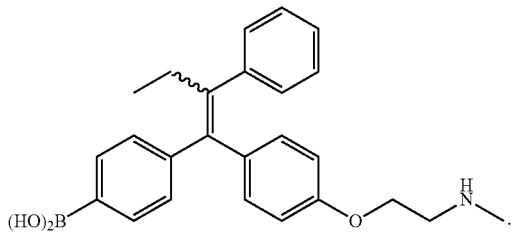 [SMILES: CCC(=C(c1ccc(OCCNC)cc1)c1ccc(B(O)O)cc1)c1ccccc1]

9. A pharmaceutical composition for the treatment of breast cancer, comprising:
a novel boron-based 4-OHT prodrug compound of Formula (I)

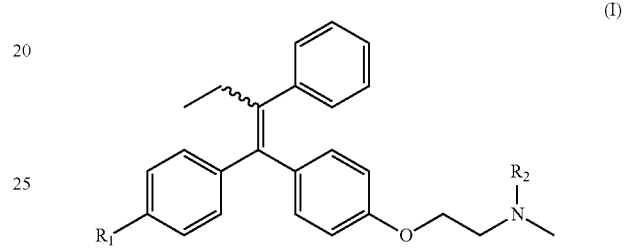

wherein
$R_1$ is

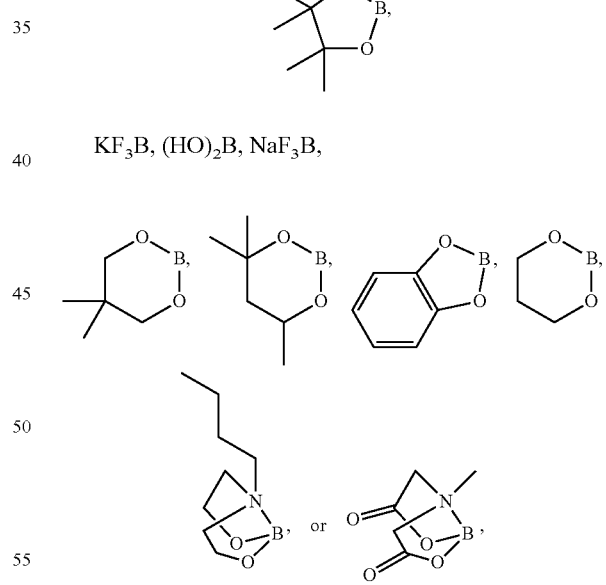

wherein the $R_1$ substituent point of attachment is on the Boron atom;
and
$R_2$ is methyl;
and
wherein said 4-OHT prodrug compound of Formula (I) is present in the composition in an amount effective for the therapeutic treatment of breast cancer.

10. The pharmaceutical composition of claim 9, wherein the novel 4-OHT prodrug is the compound N,N-Dimethyl-2-

(4-(2-phenyl-1-(4-(4,4,5,5-tetramethyl-1,3,2-dioxaborolan-2-yl)phenyl)but-1-en-1-yl)phenoxy)ethanamine.

11. The pharmaceutical composition of claim 9, wherein the novel 4-OHT prodrug is the compound Potassium (4-(1-(4-(2-(dimethylamino) ethoxy)phenyl)-2-phenylbut-1-en-1-yl)phenyl)trifluoroboronate.

12. The pharmaceutical composition of claim 9, wherein the novel 4-OHT prodrug is the compound (4-(1-(4-(2-(Dimethylamino)ethoxy)phenyl)-2-phenylbut-1-en-1-yl)phenyl) boronic acid.

13. The pharm4-OHTaceutical composition of claim 9, wherein the novel 4-OHT prodrug is the compound Sodium (4-(1-(4-(2-(dimethylamino) ethoxy)phenyl)-2-phenylbut-1-en-1-yl)phenyl)trifluoroboronate.

14. The pharmaceutical composition of claim 9, wherein the novel 4-OHT prodrug is the compound 2-(4-(1-(4-(5,5-Dimethyl-1,3,2-dioxaborinan-2-yl)phenyl)-2-phenylbut-1-en-1-yl)phenoxy)-N,N-dimethylethanamine.

15. The pharmaceutical composition of claim 9, wherein the novel 4-OHT prodrug is the compound N,N-Dimethyl-2-(4-(2-phenyl-1-(4-(4,4,6-trimethyl-1,3,2-dioxaborinan-2-yl) phenyl)but-1-en-1-yl)phenoxy)ethanamine.

16. The pharmaceutical composition of claim 9, wherein the novel 4-OHT prodrug is the compound 2-(4-(1-(4-(Benzo [d][1,3,2]dioxaborol-2-yl)phenyl)-2-phenylbut-1-en-1-yl) phenoxy)-N,N-dimethylethanamine.

17. The pharmaceutical composition of claim 9, wherein the novel 4-OHT prodrug is the compound 2-(4-(1-(4-(1,3,2-Dioxaborinan-2-yl)phenyl)-2-phenylbut-1-en-1-yl)phenoxy)-N,N-dimethylethanamine.

18. The pharmaceutical composition of claim 9, wherein the novel 4-OHT prodrug is the compound (4-(1-(4-(2-(Dimethylamino) ethoxy)phenyl)-2-phenylbut-1-en-1-yl)phenyl) N-methyliminodiacetic acid boronate.

19. The pharmaceutical composition of claim 9, wherein the novel 4-OHT prodrug is the compound (4-(1-(4-(2-(Dimethylamino) ethoxy)phenyl)-2-phenylbut-1-en-1-yl)phenyl) N-butyldiethanol amine boronate.

20. A pharmaceutical composition for the treatment of breast cancer, comprising:
    a novel boron-based endoxifen prodrug compound of Formula (I)

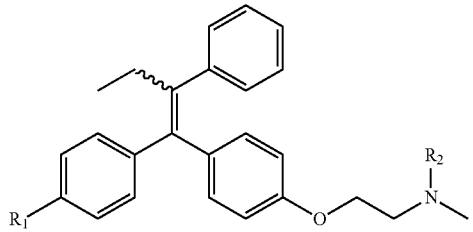

(I)

wherein
$R_1$ is

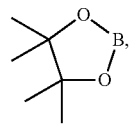

$KF_3B$, $(HO)_2B$, $NaF_3B$,

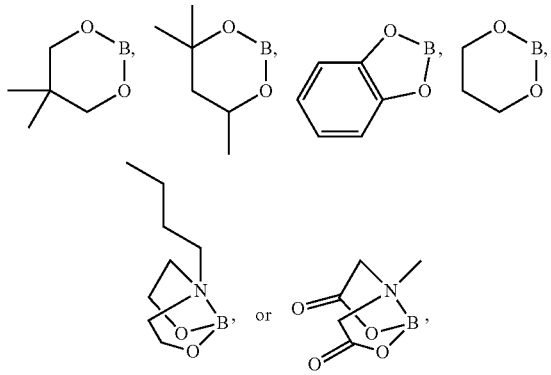

wherein the $R_1$ substituent point of attachment is on the Boron atom;
and
$R_2$ is hydrogen;
and
wherein said endoxifen prodrug compound of Formula (I) is present in the composition in an amount effective for the therapeutic treatment of breast cancer.

21. The pharmaceutical composition of claim 20, wherein the novel endoxifen prodrug is the compound (4-(1-(4-(2-(Methylamino) ethoxy)phenyl)-2-phenylbut-1-en-1-yl)phenyl)boronic acid.

22. The pharmaceutical composition of claim 20, wherein the novel endoxifen prodrug is the compound Potassium (4-(1-(4-(2-(methylamino) ethoxy)phenyl)-2-phenylbut-1-en-1-yl)phenyl)trifluoroborate.

23. The pharmaceutical composition of claim 20, wherein the novel endoxifen prodrug is the compound N-Methyl-2-(4-(2-phenyl-1-(4-(4,4,5,5-tetramethyl-1,3,2-dioxaborolan-2-yl)phenyl)but-1-en-1-yl)phenoxy)ethanamine.

24. The pharmaceutical composition of claim 20, wherein the novel endoxifen prodrug is the compound Sodium (4-(1-(4-(2-(methylamino)ethoxy)phenyl)-2-phenylbut-1-en-1-yl) phenyl)trifluoroboronate.

25. The pharmaceutical composition of claim 20, wherein the novel endoxifen prodrug is the compound 2-(4-(1-(4-(5,5-Dimethyl-1,3,2-dioxaborinan-2-yl)phenyl)-2-phenylbut-1-en-1-yl)phenoxy)-N-methylethanamine.

26. The pharmaceutical composition of claim 20, wherein the novel endoxifen prodrug is the compound N-Methyl-2-(4-(2-phenyl-1-(4-(4,4,6-trimethyl-1,3,2-dioxaborinan-2-yl) phenyl)but-1-en-1-yl)phenoxy)ethanamine.

27. The pharmaceutical composition of claim 20, wherein the novel endoxifen prodrug is the compound 2-(4-(1-(4-(Benzo[d][1,3,2]dioxaborol-2-yl)phenyl)-2-phenylbut-1-en-1-yl)phenoxy)-N-methylethanamine.

28. The pharmaceutical composition of claim 20, wherein the novel endoxifen prodrug is the compound 2-(4-(1-(4-(1, 3,2-Dioxaborinan-2-yl)phenyl)-2-phenylbut-1-en-1-yl)phenoxy)-N-methylethanamine.

29. The pharmaceutical composition of claim 20, wherein the novel endoxifen prodrug is the compound (4-(1-(4-(2-(Methylamino) ethoxy)phenyl)-2-phenylbut-1-en-1-yl)phenyl) N-methyliminodiacetic acid boronate.

30. The pharmaceutical composition of claim 20, wherein the novel endoxifen prodrug is the compound (4-(1-(4-(2-(Methylamino) ethoxy)phenyl)-2-phenylbut-1-en-1-yl)phenyl) N-butyldiethanol amine boronate.

31. The pharmaceutical composition of claim 9 in which said composition is in a form of a product for oral delivery, said product form being selected from a group consisting of a concentrate, dried powder, liquid, capsule, pellet, and pill.

32. The pharmaceutical composition of claim 9 in which said composition is in a form of a product for parenteral administration including intravenous, intradermal, intramuscular, and subcutaneous administration.

33. The pharmaceutical composition of claim 9 further comprising carriers, binders, diluents, and excipients.

34. The pharmaceutical composition of claim 20 in which said composition is in a form of a product for oral delivery, said product form being selected from a group consisting of a concentrate, dried powder, liquid, capsule, pellet, and pill.

35. The pharmaceutical composition of claim 20 in which said composition is in a form of a product for parenteral administration including intravenous, intradermal, intramuscular, and subcutaneous administration.

36. The pharmaceutical composition of claim 20 further comprising carriers, binders, diluents, and excipients.

37. A method of treating a patient for breast cancer, comprising: administering a therapeutically effective amount of the compound according to claim 1 to said patient.

38. The method according to claim 37, wherein said compound is administered in an amount ranging from about 0.001 mg/kg/day to about 1 mg/kg/day.

39. A method of preparing a compound according to claim 4, comprising synthetic steps according to the following scheme:

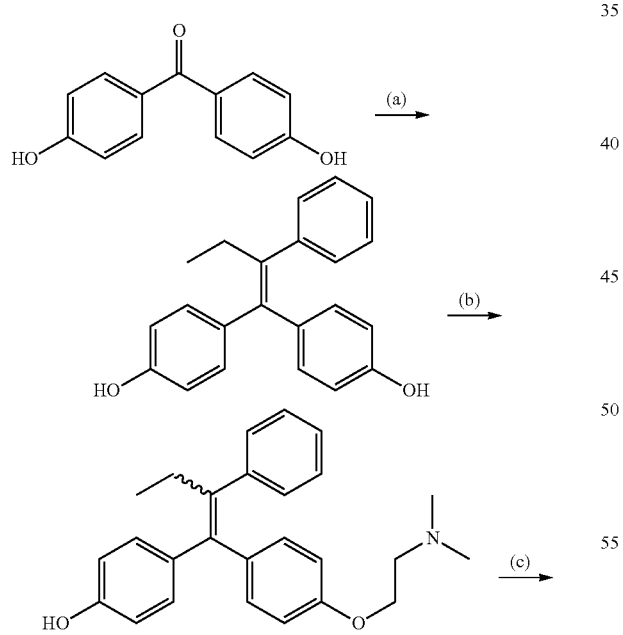

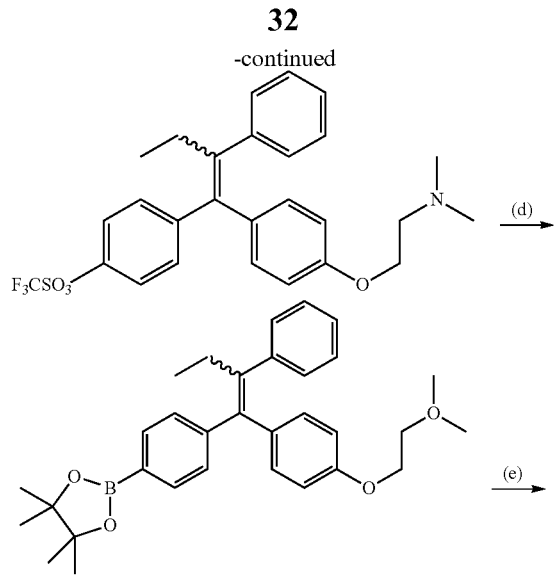

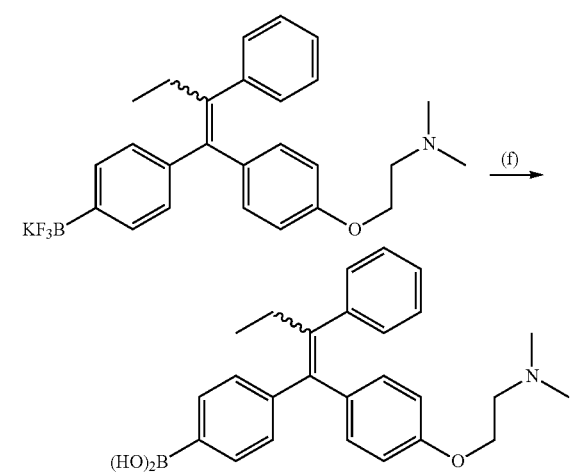

in which reagents and conditions of the scheme are as follows: (a) propiophenone, TiCl$_4$, Zn, THF, reflux; (b) 2-(dimethylamino) ethylchloride hydrochloride, Cs$_2$CO$_3$, DMF; (c) (CF$_3$SO$_2$)$_2$O, pyridine, CH$_2$Cl$_2$; (d)

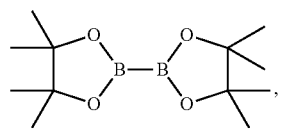

PdCl$_2$(dppf), KOAc, dioxane, reflux; (e) KHF$_2$, MeOH/H$_2$O; (f) (CH$_3$)$_3$SiCl, CH$_3$CN, H$_2$O.

40. A method of preparing a compound according to claim 8, comprising synthetic steps according to the following scheme:

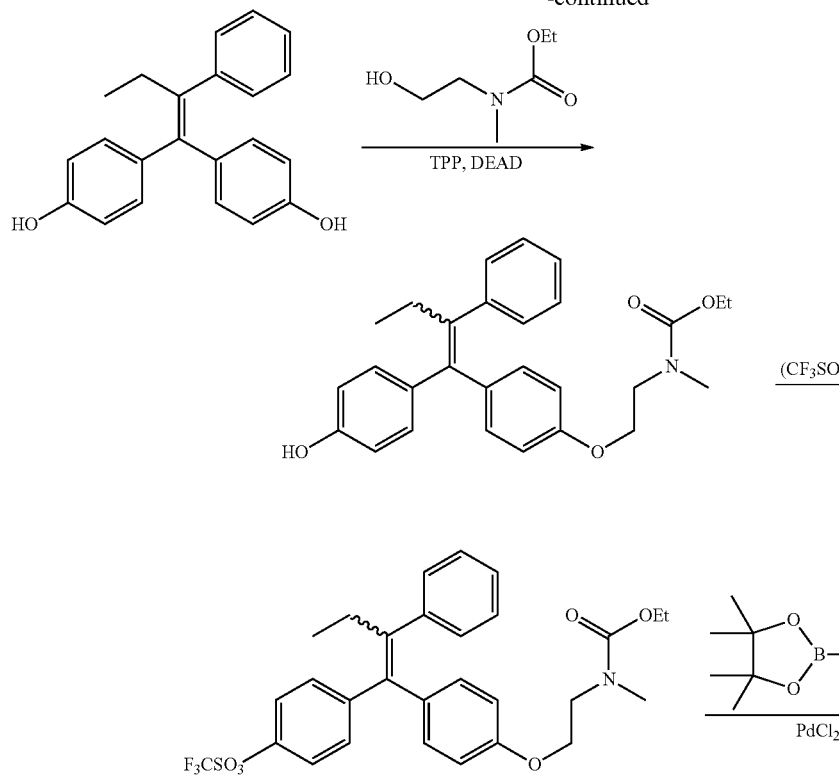
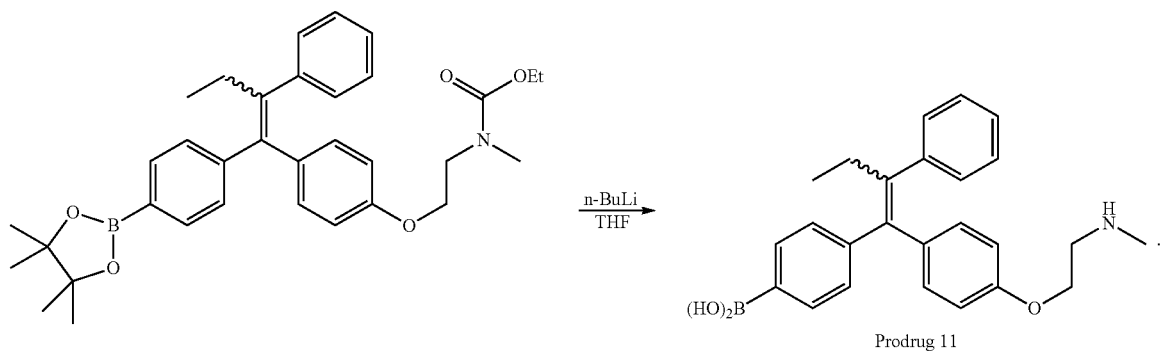
41. A method of preparing a compound according to claim 1, comprising synthetic steps according to the following scheme:
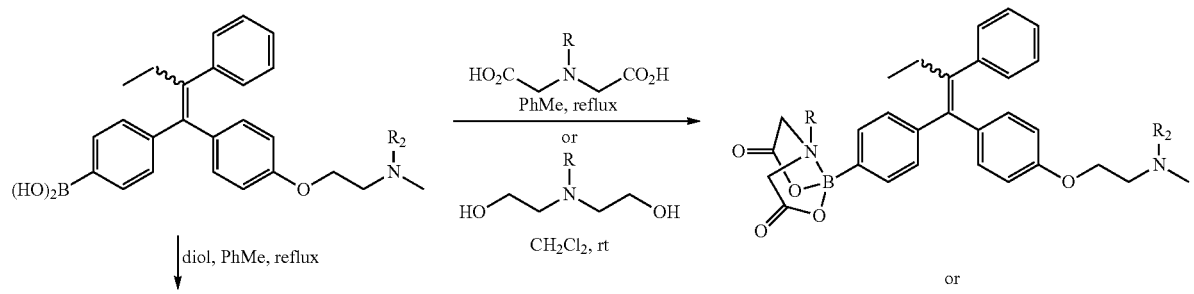

35
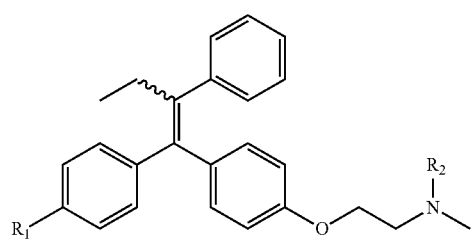
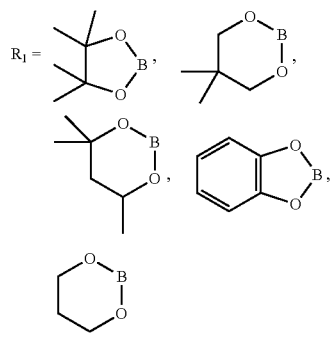
36
-continued
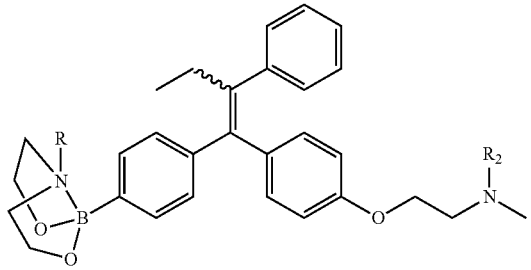
R = H, Me, Bn, n-Bu, et al.
R$_2$ = H, Me
* * * * *